(12) United States Patent
Czartoski et al.

(10) Patent No.: US 9,296,985 B2
(45) Date of Patent: *Mar. 29, 2016

(54) ALGAE BIOMASS FRACTIONATION

(75) Inventors: Thomas J. Czartoski, Dexter, MI (US); Robert Perkins, Cecil, OH (US); Jorge L. Villanueva, Dexter, MI (US); Glenn Richards, Bakersfield, CA (US)

(73) Assignee: Valicor, Inc., Dexter, MI (US)

( * ) Notice: Subject to any disclaimer, the term of this patent is extended or adjusted under 35 U.S.C. 154(b) by 700 days.

This patent is subject to a terminal disclaimer.

(21) Appl. No.: 12/963,501

(22) Filed: Dec. 8, 2010

(65) Prior Publication Data

US 2011/0086386 A1    Apr. 14, 2011

Related U.S. Application Data

(63) Continuation-in-part of application No. 12/721,077, filed on Mar. 10, 2010.

(60) Provisional application No. 61/298,401, filed on Jan. 26, 2010, provisional application No. 61/158,935, filed on Mar. 10, 2009.

(51) Int. Cl.
    *C12N 1/06*    (2006.01)
    *C12N 1/12*    (2006.01)
    *C12N 13/00*   (2006.01)

(52) U.S. Cl.
    CPC .. *C12N 1/06* (2013.01); *C12N 1/12* (2013.01); *C12N 13/00* (2013.01); *Y02E 50/17* (2013.01); *Y02E 50/343* (2013.01)

(58) Field of Classification Search
    CPC ........ C12P 5/007; C12P 9/00; C12P 2203/00; C12P 5/026; C12P 7/06; C12P 7/10; C12P 7/14; C12P 7/16; C12P 7/18; C12P 7/6427; Y02E 50/343; Y02E 50/17; Y02E 50/16; A61K 2300/00; A61K 36/00; A61K 8/97; A61K 31/66; A61K 2236/39; A61K 36/02; C12N 13/00; C12N 1/06; C12N 1/12; C12N 9/2417; C12N 9/2414; C12N 9/242; C11D 3/386; A21D 8/042; A23L 1/2753; A23L 1/2755; A23L 1/3002; C07C 29/86

See application file for complete search history.

(56) References Cited

U.S. PATENT DOCUMENTS

| | | |
|---|---|---|
| 4,417,415 A | 11/1983 | Cysewski et al. |
| 4,942,269 A * | 7/1990 | Chum et al. ................. 585/240 |
| 5,324,658 A | 6/1994 | Cox et al. |
| 5,539,133 A | 7/1996 | Kohn et al. |
| 6,166,231 A | 12/2000 | Hoeksema |
| 6,180,376 B1 | 1/2001 | Liddell |
| 6,258,964 B1 | 7/2001 | Nakajima et al. |
| 6,936,110 B2 | 8/2005 | Van Thorre |
| 2008/0155888 A1 | 7/2008 | Vick et al. |
| 2009/0004715 A1 | 1/2009 | Trimbur et al. |

FOREIGN PATENT DOCUMENTS

WO    2010000416 A1    1/2010

* cited by examiner

*Primary Examiner* — Debbie K Ware
(74) *Attorney, Agent, or Firm* — Kohn & Associates PLLC

(57) ABSTRACT

A method of fractionating biomass, by permeability conditioning biomass suspended in a pH adjusted solution of at least one water-based polar solvent to form a conditioned biomass, intimately contacting the pH adjusted solution with at least one non-polar solvent, partitioning to obtain an non-polar solvent solution and a polar biomass solution, and recovering cell and cell derived products from the non-polar solvent solution and polar biomass solution. Products recovered from the above method. A method of operating a renewable and sustainable plant for growing and processing algae.

14 Claims, 6 Drawing Sheets

ALGAE BIOMASS FRACTIONATION

BACKGROUND OF THE INVENTION

1. Field of the Invention

The present invention relates to efficiently deriving end products from biomass. In particular, the present invention relates to methods of generating end products from algae biomass and the derived products therefrom.

2. Description of the Prior Art

Biomass grown in high moisture environments such as microalgae, macroalgae, and cyanobacteria is a promising source of plant-derived primary and secondary metabolites, useful for deriving products such as biofuels and other valuable end products. In the right conditions, these aquatic organisms utilize carbon and nutrients to rapidly grow biomass containing proteins, carbohydrates, and compounds containing energy reserves in the form of long chain oxygenated hydrocarbons (such as fatty acids and glycerides—lipids) and long chain non-oxygenated hydrocarbons (such as carotenoids and waxes) and value-added organics (that have higher valued uses than fuels such as neutraceutical antioxidants) within the cellular material.

The lipids, once isolated and purified, present an excellent feedstock for a variety of liquid fuel production alternatives. Lipids fractionated from biomass can be used directly as liquid fuel feedstocks, or they can have higher value uses such as omega-3 fatty acids being used as nutritional additives. For example, biomass-derived lipids can be a viable feedstock to traditional refining operations producing products such as straight chain alkanes suitable as a direct replacement product to gasoline. Alternatively, lipids such as triglycerides can be reacted to directly form esters and selectively utilized as a biodiesel liquid fuel, replacing current edible oils being used to produce biodiesel.

The biomass metabolites traditionally not considered lipids, such as proteins and carbohydrates, have many alternative applications, including use as a feedstock for biological production systems, plastic additives (glycols from biomass sugars), use in animal nutrition as a feed, and in other fuel producing alternatives (syngas production, methane production by anaerobic digestion, ethanol production via fermentation, etc.).

Microalgae have the potential to be a major source of biofuels and biochemicals worldwide and are unique in the rapid sequestering carbon dioxide. Among other advantageous attributes, microalgae grow at a rapid pace, they are able to grow in very inhospitable conditions, they are not typically considered a human food source, and land and water use for growing microalgae is typically not competitive with land and water required for conventional food production. Microalgae production for liquid fuels and carbon sequestering is a revolutionary renewable biofuel platform. Microalgae have the potential to transform the energy industry by supplying cost transformational biofuel production systems, and novel applications of existing technologies to improve the production cost to a point competitive with fossil fuels. It is possible to produce more than ten times more oil per acre with microalgae than other biofuel crops such as palm oil.

The metabolic mechanisms of algae produce hundreds of biochemical compounds that are within the unicellular organism and typically are structurally part of the organism.

The major classes of cultivated algae and weight percentage of each class are as follows (dry weight): Lipids, triglycerides, fatty acids: 20-40%

Unsaponifiabes: non polar $C_{14}$-$C_{24}$ (10%-20%) and polar (10%-20%);

Proteins: 30%-35%.

Carbohydrates (as a blend of polysaccharides) 15%-20%.

Other—salts, organo-metallics, inorganics: 1-5%.

The challenge to algae commercialization is the total economics of land, capital equipment, operational costs, and product slate revenues. Chief among the challenges is the ability to effectively collect and isolate the valuable cell metabolites including lipids, carbohydrates, and proteins. Isolation of the compounds as opposed to comingled slurry creates value enabling concentrated streams, fuel conversion processes, and numerous focused applications of the many and varied algae metabolites.

In addition to collection and concentration of cell compounds and derivatives, critical to large-scale microalgae production is the ability to close loop residual fixed carbon, fixed nitrogen, valuable nutrients (phosphorus, potassium and trace mineral such as iron magnesium, etc) and the water. Recycling these key production ingredients is crucial to the overall energy and carbon balance for large-scale algae production operations.

Historically, high moisture biomass production systems have been designed for specific low volume product production. Prior art supplies consideration for techniques to isolate individual compounds. The prior art is predominantly focus on high value single product isolation and extraction techniques. The prior art (e.g. U.S. Pat. No. 5,539,133 to Kohn et al., U.S. Pat. No. 6,258,964 to Nakajima et al., U.S. Pat. No. 6,166,231 to Hoeksema, U.S. Pat. No. 6,180,376 to Liddell, U.S. Patent Application No. 2009/0004715 to Trimbur et al., U.S. Patent Application No. 2008/0155888 to Vick et al.) has focused on lipid fractionation. Post-lipid fractionation, the "waste" algae biomass are typically discarded or made into biogas (methane) using digesters without further fractionation of the remaining valuable products.

More specifically, U.S. Pat. No. 5,324,658 to Cox, et al. discloses a method of preparing a hydrolysate by (a) forming an aqueous slurry of algae, (b) rupturing the cell walls of the algae, (c) adding to the algae sufficient acid to form an acid concentration of about 2 to about 3M and then partially hydrolyzing proteins in the algae, (d) discarding the acid-insoluble fraction from the acid-soluble fraction of the resultant hydrolysate, (e) removing the acid from the soluble fraction until the fraction has a pH of at least about 1.0, and (f) titrating the hydrolysate with a base to convert any remaining acid in the hydrolysate to a salt and adjust the pH to within the range of about 6.5 to about 7.0. While a hydrolysate is formed, this method requires the conventional step of rupturing the cell wall before hydrolysis. This process is basically derived from the same process that is used to obtain biofuels from corn. Furthermore, while lipids can be derived from this process, the other valuable products are merely discarded because there is no fractionation involved.

U.S. Pat. No. 4,417,415 to Cysewski, et al. discloses a process for culturing microalgae and fractionating a polysaccharide therefrom. To extract the polysaccharide from the culture, the culture is brought to a pH of about 10 to about 14 and is heated to at least about 80 degrees C. for at least about 20 minutes. The culture is then cooled to not more than about 40 degrees C. and made nonalkaline with acid. After the addition of the acid, a water-miscible organic solvent is added to the culture in an amount sufficient to cause polysaccharide to precipitate therefrom and the resultant precipitated polysaccharide is separated from the accompanying liquid. Again, while polysaccharides can be fractionated, none of the other useful products are obtained because there is no fractionation.

U.S. Pat. No. 6,936,110 to Van Thorre discloses a conventional method for fractionating protein, oil and starch from grain. The method includes providing kernels or seeds comprising a germ and pericarp comprising protein, oil, and starch; steeping the kernels or seeds in a steeping reactor for a time effective to soften the kernels and seeds; milling the steeped corn kernels to separate the germ from the starch/pericarp forming a germ stream and a starch/pericarp stream; subjecting the germ to rapid pressurization/depressurization in order to extract oil and protein from the germ; and separating the starch from the pericarp. This is a typical wet milling process that can be employed for algae as well; however, it is a high energy process and requires substantial modifications in order to be used with algae.

WO/2010/000416 to D'Addario, et al. describes the extraction of fatty acids from algal biomass comprising: producing an aqueous suspension of algal biomass; subjecting the aqueous suspension of algal biomass to acid hydrolysis and extraction by the addition of at least one non-polar organic solvent and at least one inorganic acid under atmospheric pressure to said aqueous suspension of algal biomass, so as to obtain the following three phases: (i) a semisolid phase comprising a slurry of the algal biomass; (ii) an aqueous phase comprising inorganic compounds and hydrophilic organic compounds; (iii) an organic phase comprising fatty acids and hydrophobic organic compounds other than said fatty acids. It is required that the solvent and the acid be added at the same time and that the process be performed at a temperature below 100° C. By combining and limiting these operating conditions, WO/2010/000416 cannot fully extract the cell products from the algal biomass.

State-of-the-art patents tend to focus on specific classes of products such as lipids or polysaccharides or specific products such as DHA as specific polyunsaturated fatty acid. State-of-the-art patents tend not to address at all fractionation platforms addressing the practical need of not only isolating the target classes or product but addressing the need for recovering and or using all non-target materials.

Therefore, there is not only a need for an efficient and inexpensive method of raising algae, but there is a need for an efficient and flexible fractionation platform that can achieve success at isolating classes and specific products and in addition recover on a large scale all valuable products efficiently from the algal biomass.

A novel fractionation platform is articulated as the present invention that is a paradigm shift away from the prior art as it allows not only extraction of target classes and products but to recovery by-products and recycle critical nutrients and water. The present invention provides for a flexible and efficient fractionation platform that will allow not only targeted product isolation and preconditioning the products, but by-products to be effectively separated as classes and specific products with ultimately even nutrients and water to be recycled.

SUMMARY OF THE INVENTION

The present invention provides for a method of fractionating biomass, including the steps of: permeating walls of biomass cells, liberating cell products from the cells, and fractionating and recovering the liberated cell products and derivatives.

The present invention provides for a method of fractionating biomass, including the steps of: permeability conditioning biomass suspended in a pH adjusted solution of at least one water-based polar solvent to form a conditioned biomass, intimately contacting the conditioned biomass with at least one non-polar solvent, partitioning to obtain a non-polar solvent solution and a polar biomass solution, and recovering cell products from the non-polar solvent solution and polar biomass solution.

The present invention also provides for products recovered from the above method in the non-polar solvent solution, chosen from the group consisting of lipid products, hydrocarbon chains, and organic compounds.

The present invention provides for products recovered from the above method in the polar biomass solution, chosen from the group consisting of soluble monosaccharides, disaccharides, oligosaccharides, polysaccharides, glycerols, amino acids, soluble proteins, peptides, fiber, nutrients, phosphocholine, phosphate, growth media, and residual solid algae cell structural particles.

The present invention provides for products recovered from the above method in the polar biomass solution, chosen from the group consisting of alcohols and carbon dioxide.

The present invention provides for products recovered from the above method in the polar biomass solution of primary and secondary macronutrients and micronutrients chosen from the group consisting of phosphorous, nitrogen, potassium, calcium, sulfur, magnesium, boron, chlorine, manganese, iron, zinc, copper, molybdenum, and selenium.

The present invention further provides for a method of fractionating biomass, including the steps of: permeability conditioning biomass suspended in a pH adjusted solution of at least one water-based polar solvent to form a conditioned biomass, intimately contacting the conditioned biomass with at least one non-polar solvent and an alcohol and simultaneously transesterifying acylglycerols and esterifying free fatty acids, partitioning to obtain an non-polar solvent solution and a polar biomass solution, and recovering cell and cell derivative products from the non-polar solvent solution and polar biomass solution.

The present invention provides for a method of fractionating biomass, including the steps of: permeability conditioning biomass suspended in a pH adjusted solution of at least one water-based polar solvent to form a conditioned biomass, intimately contacting the conditioned biomass with at least one non-polar solvent and an alcohol and simultaneously transesterifying acylglycerols and esterifying free fatty acids, partitioning to obtain an non-polar solvent solution and a polar biomass solution, fermenting the polar biomass solution, and recovering alcohol, acylglycerols, and free fatty acids.

The present invention provides for a method of fractionating biomass, including the steps of: permeability conditioning biomass suspended in a pH adjusted solution of at least one water-based polar solvent to form a conditioned biomass, intimately contacting the conditioned biomass with at least one organic solvent, partitioning to obtain an non-polar solvent solution and a polar biomass solution, concentrating valuable compounds dissolved and suspended within the polar biomass solution resulting in a concentrated solution, providing for supplemental fixed carbon nutrients via liquification and saccrification of residual biomass solids by beneficial use of process acid waters and/or enzymatic hydrolysis, and obtaining a concentrated supplemented media solution.

The present invention also provides for a method of utilizing the concentrated supplemented media solution for biological growth or fermentation production systems as obtained in the above method.

The present invention provides for a method of fractionating biomass, including the steps of: permeability conditioning biomass suspended in a pH adjusted solution of at least one water-based polar solvent to form a conditioned biomass, intimately contacting the conditioned biomass with at least one non-polar solvent, partitioning to obtain an non-polar solvent solution and a polar biomass solution, and utilizing a concentrated polar biomass solution as a growth media with an organism chosen from the group consisting of a mixotroph, heterotroph, or chemautroph.

The present invention provides for a method of fractionating biomass, including the steps of: permeability conditioning biomass suspended in a pH adjusted solution of at least one water-based polar solvent to form a conditioned biomass, intimately contacting the conditioned biomass with at least one non-polar solvent, partitioning to obtain an non-polar solvent solution and a polar biomass solution, concentrating the polar biomass solution, biologically digesting or fermenting the water based polar solution, and repeating the fractionation process to obtain additional cell products and cell derived products.

The present invention provides for a method of operating a renewable and integrated sustainable processing plant for growing and processing algae, including the steps of: growing algae, harvesting the algae, permeability conditioning biomass suspended in a pH adjusted solution of at least one water-based polar solvent to form a conditioned biomass and liberating cell products from within the algae, intimately contacting the conditioned biomass with at least one non-polar solvent, partitioning to obtain an non-polar solvent solution and a polar biomass solution, obtaining growth media from the polar biomass solution and carbon dioxide from the polar biomass solution, and recycling the carbon dioxide and growth media to the algae cultivation system for renewable and sustainable operation.

The present invention provides for a method of fractionating biomass, including the steps of: permeability conditioning biomass suspended in a pH adjusted solution of at least one water-based polar solvent to form a conditioned biomass, intimately contacting the conditioned biomass with at least one non-polar solvent, partitioning to obtain an non-polar solvent solution and a polar biomass solution, converting organic phosphorus into inorganic phosphate, and recovering the inorganic phosphate.

The present invention also provides for a method of fractionating biomass, including the steps of: permeability conditioning biomass suspended in a pH adjusted solution of at least one water-based polar solvent to form a conditioned biomass, intimately contacting the conditioned biomass with at least one non-polar solvent, partitioning to obtain an non-polar solvent solution and a polar biomass solution, and obtaining biocrude.

The present invention provides for biocrude obtained from the above method.

BRIEF DESCRIPTION OF THE DRAWINGS

Other advantages of the present invention will be readily appreciated as the same becomes better understood by reference to the following detailed description when considered in connection with the accompanying drawings, wherein.

DETAILED DESCRIPTION

Figure 1:
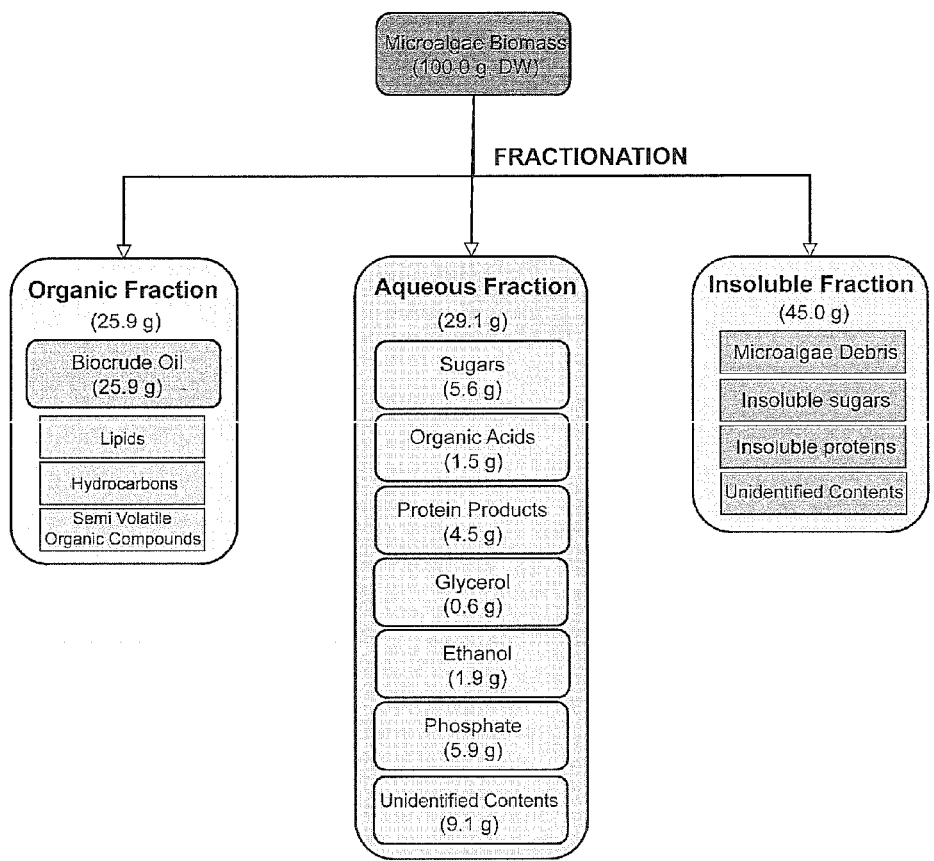
FIG. 1 is a chart illustrating the fractionated products from microalgae biomass using this invented fractionation process.

The present invention provides generally for a process of fractionating the major components of biomass containing membrane-bound lipids on a large scale. Most generally, the process involves liberating cell products, separating the products by phases, and fractionating multiple metabolites from biomass. Unlike prior art processes that use high energy disruption followed by general lipid extraction to extract a single product, the present invention provides a fractionation process, made possible by a conditioning process, a contacting process, and a partitioning process described in greater detail below. The process optionally includes various steps to form fatty esters and convert additional products of the biomass fractionation for use. Throughout the application, the biomass is more specifically referred to as "algae" or "microalgae"; however, it should be understood that the biomass can be any composition further described below in the definitions.

As used herein, the terms "fractionate," "fractionating," "fractioned" or "fractionation," when used in conjunction with the fractionation of oil from a biomass, mean the removal of lipids from the cells of the biomass, whether those lipids remain associated with the cells from which they were derived or not. Thus, the term "fractionating" or its related forms can mean removing the oil from the cells to form a mixture comprising isolated lipids and cellular material, or it can be used to mean physically isolating and separating the lipids from the cellular material.

"Polar" as used herein refers to a compound that has portions of negative and/or positive charges forming negative and/or positive poles. While a polar compound does not carry a net electric charge, the electrons are unequally shared between the nuclei. Water is considered a polar compound in the present invention.

"Non-polar" as used herein refers to a compound that has no separation of charge, and so no positive or negative poles are formed. An example of a non-polar compound is an alkane in the present invention.

"Miscible" as used herein refers to a compound that can fully mix with a fluid. "Water-miscible" refers to a compound that is fully mixable with water.

"Hydrophilic" as used herein refers to a compound that is charge-polarized and capable of hydrogen bonding, i.e. polar, allowing it to dissolve readily in water.

"Hydrophobic" as used herein refers to a compound that is repelled from water and tends to be non-polar and prefer other neutral molecules or non-polar molecules.

"Oil" as used herein refers to any combination of fractionable lipid fractions of a biomass. "Lipid," "lipid fraction," or "lipid component" as used herein can include any hydrocarbon soluble in non-polar solvents and insoluble, or relatively insoluble, in water. The fractionable lipid fractions can include, but are not limited to, free fatty acids, waxes, sterols and sterol esters, triacylglycerols, diacylglycerides, monoacylglycerides, tocopherols, eicosanoids, glycoglycerolipids, glycosphingolipids, sphingolipids, and phospholipids. The lipid fractions can also comprise other liposoluble materials such as chlorophyll and other algal pigments, including, for example, antioxidants such as astaxanthins.

"Membrane-bound lipids", as recited herein, refers to any lipid attached to or associated with the membrane of a cell or the cell wall, or with the membrane of any organelle within the cell. While the present invention provides methods for fractionating membrane-bound lipids, it is not so limited. The present invention can be used to fractionate intracellular lipids (e.g., lipids retained with the cell wall or in vacuoles) or extracellular lipids (e.g. secreted lipids), or any combination of intracellular, extracellular, cell wall bound, and/or membrane-bound lipids.

"Biomass" is used to refer to any living or recently dead biological cellular material derived from plants or animals. In certain embodiments, biomass can be selected from the group consisting of fungi, bacteria, yeast, mold, and microalgae. In other embodiments, the biomass can be agricultural products, such as corn stalks, straw, seed hulls, sugarcane leavings, bagasse, nutshells, and manure from cattle, poultry, and hogs, wood materials, such as wood or bark, sawdust, timber slash, and mill scrap, municipal waste, such as waste paper and yard clippings, or crops, such as poplars, willows, switchgrass, alfalfa, prairie bluestem, corn, and soybean. In certain embodiments, the biomass used with the invention is derived from plants.

Any biomass as defined herein can be used with the methods of the invention. In certain embodiments, the biomass is selected from the group consisting of fungi, bacteria, yeast, mold, and microalgae. The biomass can be naturally occurring, or it can be genetically modified to enhance lipid production. In a preferred embodiment, the biomass is microalgae. The present invention can be practiced with any microalgae. The microalgae can be grown in a closed system, such as a bioreactor, or it can be grown in open ponds. The microalgae can be grown with or without sunlight (autotrophically or heterotrophically) and with many varied carbon sources. The microalgae used with the invention can include any naturally occurring species or any genetically engineered microalgae. In particular, the microalgae can be genetically engineered to have improved lipid production characteristics, including but not limited to optimizing lipid yield per unit volume and/or per unit time, carbon chain length (e.g., for biodiesel production or for industrial applications requiring hydrocarbon feedstock), reducing the number of double or triple bonds, optionally to zero, removing or eliminating rings and cyclic structures, and increasing the hydrogen:carbon ratio of a particular species of lipid or of a population of distinct lipids. In addition, microalgae that naturally produce appropriate hydrocarbons can also be engineered to have even more desirable hydrocarbon outputs. The microalgae can be grown in freshwater, brackish water, brines, or saltwater. The microalgae used with the invention include any commercially available strain, any strain native to a particular region, or any proprietary strain. Additionally, the microalgae can be of any Division, Class, Order, Family, Genus, or Species, or any subsection thereof. Combinations of two or more microalgae also fall within the scope of the invention.

Microalgae can be harvested by any conventional means (including, but not limited to filtration, air flotation and centrifugation) and the algal paste generated by concentrating the harvested microalgae to the desired weight % of solids. In some instances, the desired weight % of solids can be achieved by adding a solvent, preferably a polar solvent, to a batch of microalgae having a higher than desired weight % of solids. For example, this practice can be useful when it is desired to reuse the recycled polar solvent from a prior fractionation.

In certain embodiments, the microalgae used with the methods of the invention are members of one of the following divisions: Chlorophyta, Cyanophyta (Cyanobacteria), and Heterokontophyta. In certain embodiments, the microalgae used with the methods of the invention are members of one of the following classes: Bacillariophyceae, Eustigmatophyceae, and Chrysophyceae. In certain embodiments, the microalgae used with the methods of the invention are members of one of the following genera: *Nannochloropsis, Chlorella, Dunaliella, Scenedesmus, Selenastrum, Oscillatoria, Phormidium, Spirulina, Amphora*, and *Ochromonas*.

Non-limiting examples of microalgae species that can be used with the methods of the present invention include: *Achnanthes orientalis, Agmenellum* spp., *Amphiprora hyaline, Amphora coffeiformis, Amphora coffeiformis* var. *linea, Amphora coffeiformis* var. *punctata, Amphora coffeiformis* var. *taylori, Amphora coffeiformis* var. *tenuis, Amphora delicatissima, Amphora delicatissima* var. *capitata, Amphora* sp., *Anabaena, Ankistrodesmus, Ankistrodesmus falcatus, Boekelovia hooglandii, Borodinella* sp., *Botryococcus braunii, Botryococcus sudeticus, Bracteococcus minor, Bracteococcus medionucleatus, Carteria, Chaetoceros gracilis, Chaetoceros muelleri, Chaetoceros muelleri* var. *subsalsum, Chaetoceros* sp., *Chlamydomas perigranulata, Chlorella anitrata, Chlorella antarctica, Chlorella aureoviridis, Chlorella candida, Chlorella capsulate, Chlorella desiccate, Chlorella ellipsoidea, Chlorella emersonii, Chlorella fusca, Chlorella fusca* var. *vacuolata, Chlorella glucotropha, Chlorella infusionum, Chlorella infusionum* var. *actophila, Chlorella infusionum* var. *auxenophila, Chlorella kessleri, Chlorella lobophora, Chlorella luteoviridis, Chlorella luteoviridis* var. *aureoviridis, Chlorella luteoviridis* var. *lutescens, Chlorella miniata, Chlorella minutissima, Chlorella mutabilis, Chlorella nocturna, Chlorella ovalis, Chlorella parva, Chlorella photophila, Chlorella pringsheimii, Chlorella protothecoides, Chlorella protothecoides* var. *acidicola, Chlorella regularis, Chlorella regularis* var. *minima, Chlorella regularis* var. *umbricata, Chlorella reisiglii, Chlorella saccharophila, Chlorella saccharophila* var. *ellipsoidea, Chlorella salina, Chlorella simplex, Chlorella sorokiniana, Chlorella* sp., *Chlorella sphaerica, Chlorella stigmatophora, Chlorella vanniellii, Chlorella vulgaris, Chlorella vulgaris* fo. *tertia, Chlorella vulgaris* var. *autotrophica, Chlorella vulgaris* var. *viridis, Chlorella vulgaris* var. *vulgaris, Chlorella vulgaris* var. *vulgaris* fo. *tertia, Chlorella vulgaris* var. *vulgaris* fo. *viridis, Chlorella xanthella, Chlorella zofingiensis, Chlorella trebouxioides, Chlorella vulgaris, Chlorococcum infusionum, Chlorococcum* sp., *Chlorogonium, Chroomonas* sp., *Chrysosphaera* sp., *Cricosphaera* sp., *Crypthecodinium cohnii, Cryptomonas* sp., *Cyclotella cryptica, Cyclotella meneghiniana, Cyclotella* sp., *Dunaliella* sp., *Dunaliella bardawil, Dunaliella bioculata, Dunaliella granulate, Dunaliella maritime, Dunaliella minuta, Dunaliella parva, Dunaliella peircei, Dunaliella primolecta, Dunaliella salina, Dunaliella terricola, Dunaliella tertiolecta, Dunaliella viridis, Dunaliella tertiolecta, Eremosphaera viridis, Eremosphaera* sp., *Ellipsoidon* sp., *Euglena* spp., *Franceia* sp., *Fragilaria crotonensis, Fragilaria* sp., *Gleocapsa* sp., *Gloeothamnion* sp., *Haematococcus pluvialis, Hymenomonas* sp., *Isochrysis aff. galbana, Isochrysis galbana, Lepocinclis, Micractinium, Micractinium, Monoraphidium minutum, Monoraphidium* sp., *Nannochloris* sp., *Nannochloropsis salina, Nannochloropsis* sp., *Navicula acceptata, Navicula biskanterae, Navicula pseudotenelloides, Navicula pellic020losa, Navicula saprophila, Navicula* sp., *Nephrochloris* sp., *Nephroselmis* sp., *Nitschia communis, Nitzschia alexandrina, Nitzschia closterium, Nitzschia communis, Nitzschia dissipata, Nitzschia frustulum, Nitzschia hantzschiana, Nitzschia inconspicua, Nitzschia intermedia, Nitzschia microcephala, Nitzschia pusilla, Nitzschia pusilla elliptica, Nitzschia pusilla monoensis, Nitzschia quadrangular, Nitzschia* sp., *Ochromonas* sp., *Oocystis parva, Oocystis pusilla, Oocystis* sp., *Oscil-*

*latoria limnetica*, *Oscillatoria* sp., *Oscillatoria subbrevis*, *Parachlorella kessleri*, *Pascheria acidophila*, *Pavlova* sp., *Phaeodactylum tricomutum*, *Phagus*, *Phormidium*, *Platymonas* sp., *Pleurochrysis carterae*, *Pleurochrysis dentate*, *Pleurochrysis* sp., *Prototheca wickerhamii*, *Prototheca stagnora*, *Prototheca portoricensis*, *Prototheca moriformis*, *Prototheca zopfii*, *Pseudochlorella aquatica*, *Pyramimonas* sp., *Pyrobotrys*, *Rhodococcus opacus*, *Sarcinoid chrysophyte*, *Scenedesmus armatus*, *Schizochytrium*, *Spirogyra*, *Spirulina platensis*, *Stichococcus* sp., *Synechococcus* sp., *Synechocystisf*, *Tagetes erecta*, *Tagetes patula*, *Tetraedron*, *Tetraselmis* sp., *Tetraselmis suecica*, *Thalassiosira weissflogii*, and *Viridiella fridericiana*.

In certain embodiments, the biomass can be wild type or genetically modified yeast. Non-limiting examples of yeast that can be used with the present invention include *Cryptococcus curvatus*, *Cryptococcus terricolus*, *Lipomyces starkeyi*, *Lipomyces lipofer*, *Endomycopsis vernalis*, *Rhodotorula glutinis*, *Rhodotorula gracilis*, *Candida* 107, *Saccharomyces paradoxus*, *Saccharomyces mikatae*, *Saccharomyces bayanus*, *Saccharomyces cerevisiae*, any *Cryptococcus*, *C. neoformans*, *C. bogoriensis*, *Yarrowia lipolytica*, *Apiotrichum curvatura*, *T. bombicola*, *T. apicola*, *T. petrophilum*, *C. tropicalis*, *C. lipolytica*, and *Candida albicans*.

In certain embodiments, the biomass can be a wild type or genetically modified fungus. Non-limiting examples of fungi that can be used with the present invention include *Mortierella*, *Mortierrla vinacea*, *Mortierella alpine*, *Pythium debaryanum*, *Mucor circinelloides*, *Aspergillus ochraceus*, *Aspergillus terreus*, *Pennicillium iilacinum*, *Hensenulo*, *Chaetomium*, *Cladosporium*, *Malbranchea*, *Rhizopus*, and *Pythium*.

In other embodiments, the biomass can be any bacteria that generate lipids, proteins, and carbohydrates, whether naturally or by genetic engineering. Non-limiting examples of bacteria that can be used with the present invention include *Escherichia coli*, *Acinetobacter* sp. any actinomycete, *Mycobacterium tuberculosis*, any streptomycete, *Acinetobacter calcoaceticus*, *P. aeruginosa*, *Pseudomonas* sp., *R. erythropolis*, *N. erthopolis*, *Mycobacterium* sp., *B.*, *U. zeae*, *U. maydis*, *B. lichenformis*, *S. marcescens*, *P. fluorescens*, *B. subtilis*, *B. brevis*, *B. polmyma*, *C. lepus*, *N. erthropolis*, *T. thiooxidans*, *D. polymorphis*, *P. aeruginosa* and *Rhodococcus opacus*.

As used herein, "hydrated biomass" refers to biomass comprising, at minimum, 50% by weight of polar solvent. The solvent can include both intracellular and extracellular solvent. In certain embodiments, the solvent is a polar solvent, preferably water or a mixture of water and one or more other polar solvents. The polar solvent is polar relative to a non-polar solvent further described below. In some embodiments, solvent, for example a polar solvent such as, but not limited to, low molecular weight aldehydes, ketones, fatty acids, methanol, ethanol, amyl alcohols, propanols, butanols, formic acid, acetic acid, propionic acid, and amphipathic solvents, can be added to an aliquot of biomass in a given form to achieve a particular biomass to solvent ratio.

In certain embodiments, the hydrated biomass comprises at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or at least about 99.5% by weight of a polar solvent or mixture of polar solvents. In other embodiments, the hydrated biomass comprises below about 99.5%, below about 99%, below about 98%, below about 97%, below about 96%, below about 95%, below about 94%, below about 93%, below about 92%, below about 91%, below about 90%, below about 85%, below about 80%, below about 75%, below about 70%, below about 65%, or below about 60% by weight of a polar solvent or mixture of polar solvents. It will also be understood that in accordance with the invention, the weight percent of the polar solvent or mixture of polar solvents in the hydrated biomass can be within inclusive ranges of the limits recited above. For example, the weight percent of the polar solvent or mixture of polar solvents can fall within one or more of the following inclusive ranges: between about 50% to about 99.5%, between about 60% and about 95%, between about 60% and about 80%, between about 60% and about 70%, between about 70% and about 80%, between about 75% and about 99%, between about 85% and about 95%, between about 90% and about 95%, or between about 90% and about 93%.

Where the hydrated biomass comprises microalgae, the microalgae can be in the form of an algal paste. In certain embodiments of the invention, the algal paste (or the hydrated biomass) can comprise about 0.5%, about 1%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 30%, about 35%, or about 40% solids by weight. Additionally, it will be understood by one of skill in the art that the % solids of the algal paste can be within inclusive ranges of the limits recited above. Thus, in certain embodiments, the algal paste can comprise about 1-25% solids, about 1-20% solids, about 2-15% solids, about 5-10% solids, about 5-15% solids about 3-20% solids, about 5-20% solids, about 5-25% solids, about 5-15% solids, about 7-10% solids, about 8-10% solids, about 9-10% solids, about 7-8% solids, about 7-9% solids, or about 8-9% solids by weight.

Consumption of acid and corresponding neutralization caustic can be minimized by processing concentrated or dewatered algae and discharging concentrated slurry while reusing the more dilute conditioning agent.

As used herein, unless otherwise specified, the term "about" precedes a numerical value, the numerical value is understood to mean the stated numerical value and also ±10% of the stated numerical value.

"Conditioning" the hydrated biomass as used herein refers to disturbing the integrity of the cell walls in any manner or combination of manners that transforms them into any state wherein the lipids and other cell products contained therein are made more accessible to solvents, i.e. the cell products are "liberated". "Conditioning" can also be referred to as "permeability conditioning", as the conditioning affects the permeability of the cell walls. As used herein "disordered cellular material" refers to a cell or cells that have been modified to any state or combination of states wherein the lipids contained therein are made more accessible to solvents. In other words, disordered cellular material includes cells that have been physically, chemically, or biologically altered, but not necessarily disrupted, to achieve maximum exposure of cell surfaces and internal cell moieties to polar and non-polar solvent penetration. In accordance with the invention, the cells of the hydrated biomass need not be lysed, although they can be. In some non-limiting examples, the cells can be fragmented, partially fragmented, or unfragmented; the plasma membrane can be weakened and/or disrupted; the cell wall can be weakened and/or disrupted; or the cells can exist in a combination of such states. Thus, the cells of the biomass can be disrupted, not disrupted, or partially disrupted. In certain embodiments, where cell disruption occurs, less than about 70%, less than about 60%, less than about 50%, less than about 40%, less than about 30%, less than about 20%, or less than about 10% cell breakage occurs.

In accordance with the methods of the invention, the hydrated algae biomass from which metabolites are fractionated is first conditioned to create a disordered cellular material. Unlike prior high energy physical disruption, this conditioning step serves to disorder and dissociate the metabolite compounds from the cell walls and membranes and other lipid-containing cellular material. Essentially, the cell walls of the algae are chemically permeated to liberate cell products. The cell walls can have a waxy protective outer layer that must be permeated in order to obtain the cell products therein. While not intending to be bound by any theory, it is believed that conditioning (by any techniques or conditions or combinations thereof) the hydrated biomass erodes and softens the outer layer of the cells by digesting or deteriorating a portion of the complex cell wall structure, as well as other parts of the cell, enabling solvent permeation, penetration, and access to the cell membrane and interior of the cell, specifically to the lipids, proteins, and carbohydrates contained therein. This allows the various components such as lipids and other cell products inside the cell become soluble within the respective miscible fluid, facilitating fraction and subsequent isolation. This step is analogous to what happens inside varieties of fish's stomach that eat algae, as these fish are able to digest algae to obtain the nutrients therein.

This conditioning step is much different than the presently used method in the art of lysing the algae cells, which requires drying the algae biomass and bursting the algae cells to obtain the lipids therein. In the present invention, the cell wall remains intact or partially disrupted (10%-50%) but allows for materials to be liberated for collection and further fractionation. Currently used methods in the prior art were adopted from the method of extracting oil from soybeans without fully understanding the composition and specific properties of algae. The method of the present invention is designed for any biomass, and specifically works well for algae, and the present method would not work on soybeans, unlike the methods of the prior art. The method of the present invention is also a low energy method, as opposed to the high energy required to obtain the lipids in the prior art.

"Liberating" as used herein, refers to freeing various cell products such as lipids from the cell wall of a particular biomass. As stated above, the cell wall, especially in algae, is very strong and includes a waxy outer layer. Previous methods of extracting cell metabolites break the cell walls to access metabolites inside the cell but do not actually free the metabolites that are trapped within the cell walls. By conditioning the biomass as described above, the present invention is able to liberate cell products that are otherwise not accessible. The conditioning step is an erosive, corrosive, and digestive process that degrades the outer cell wall. Cell products can be further liberated by accelerating the conditioning step as further described below by adding enzymes to the biomass and performing electromagnetic pulsing. Unlike previous methods, these accelerators do not break down the cell wall itself but allow access to the inner cell wall in order to liberate cell products.

As used herein, "suspension" refers to a heterogeneous mixture of substances; use of the term "suspension" is not intended to imply or limit the invention to any particular physical arrangement of particles and/or components within the heterogeneous mixture.

As used herein, "cellular debris" refers to those portions of the biomass which remain in a solid or solvent insoluble condition. These are typically particles that can be readily separated from the solvent mixtures by means such as filtration or weight differential centrifugation.

As used herein, "water soluble compounds" are chemical constituents or fragments that are soluble in polar solvent, including, for example, soluble inorganic compounds such as acids, cations, anions, salts, and soluble organic compounds such as simple sugars, amino acids, and proteins.

Most generally, a method of fractionation of biomass such as algae having cell walls is provided in the present invention by permeating the biomass cell walls, liberating cell products from the cells, and fractionating and recovering the liberated cell products. More specifically, this method involves permeability conditioning biomass suspended in a pH adjusted solution of at least one water-based polar solvent to form a conditioned biomass, forcing intimate contacting of an non-polar solvent with the conditioned biomass, partitioning to obtain a polar biomass solution with soluble compounds and cellular debris as well as an non-polar solvent solution. This process is shown generally in the flow diagram in FIGS. 1 and 2. Once the polar biomass solution and non-polar solvent solution have been obtained, these solutions can be further processed (i.e. fractionated) to recover and obtain additional products as described below. In other words, both cell products and cell derived products can be recovered from the biomass.

The kinetics of the fractionation involves the following. The permeability conditioning allows for fractionation of polar and water soluble components from the biomass. The intimately contacting with an non-polar solvent draws out hydrophobic components such as lipids. The partitioning separates the water soluble phase from the solvent soluble phase as well as a layer of cellular debris, all of which can be fractionated further to derive various products described below.

It should be understood that when the biomass is algae, that different species or particular batches can have different properties. Therefore, the present invention allows for a user to modify various conditions of the process, such as, but not limited to, temperature, time, pH, solvents, or particular methods used in order to both adjust for the particular algae and to maximize and/or minimize the fractions produced.

More specifically, the permeability conditioning step includes adding an acid or a base to the biomass hydrolyzed with water. This step serves to improve cell wall permeability and solubilize valuable carbohydrates and proteins to liberate the cell products from the cell. This is a mild hydrolysis, and possibly not considered by one skilled in the art a "true" hydrolysis. During the conditioning step, sugars and other water-soluble cellular components are immediately fractionated into the conditioning liquid (the added acid/base and water from the biomass), and thus fractionation of the biomass begins immediately upon conditioning.

Conditioning of the hydrated biomass (or the algal paste where used) to create a disordered cellular material can be performed by any means known in the art such as those previously described above, including, but not limited to, exposure to heat, exposure to a pH adjusting agent (acidic agents and alkali agents), enzymatic treatment (including, but not limited to, treatment with a cellulase, treatment with a protease, treatment with a lipase, or treatment with any combination of these), mechanical treatment (including, but not limited to, shear mixers, colloid mills, and homogenization), osmotic shock, infection with a lytic virus, or any combination or combinations thereof. In other embodiments, conditioning of the hydrated biomass can be achieved by exposing the biomass to elevated pressure in addition to treatment with one or more of the methods previously recited.

In certain embodiments, the pH adjusting agent comprises a base. In certain embodiments where the pH adjusting agent is a base, a sufficient amount of pH adjusting agent is added to the biomass to reach a solution pH of about 8.0, of about 9.0, of about 10.0, of about 11.0, of about 12.0, or of about 13.0. In general, the pH is preferably changed to a range of 7.5 to 14. The base is preferably, but not limited to, sodium hydroxide, potassium hydroxide, calcium hydroxide, and other metal hydroxides from the alkali metals and alkaline earth metals, ammonium hydroxide, ammonia, sodium carbonate, potassium carbonate, boron hydroxide, aluminum hydroxide, borax, amino alcohols such as ethanol amine, diethanolamine, triethanol amine, isopropanolamine, diisopropylamine, triisopropylamine, propylamine, 2-propylamine, methylamine, dimethylamine, trimethylamine, dimethylethanol amine, monomethylethanolamine, 2-(2-aminoethoxy)ethanol, diglycolamines, diethylamine and other similar polyamines, or a mixture thereof.

When an acid is used in the conditioning step, the pH of the biomass is preferably changed to a range of 1.0 to 6.5. A stronger acid can provide a higher yield of cellular metabolite fractions overall, as demonstrated in Examples 3 and 10. Preferably, the pH adjusting agent is selected from the group consisting of an organic acid, a mineral acid, or a mixture thereof. The pH adjusting agent can also be an acid including, but not limited to, acetic acid, hydrochloric acid, nitric acid, phosphoric acid, sulfuric acid, boric acid, hydrofluoric acid, hydrobromic acid, or a mixture of one or more of the recited acids. In a preferred embodiment the pH adjusting agent is a mixture of sulfuric acid and phosphoric acid. The mixture can be in any ratio, including but not limited to about 10% sulfuric acid and about 90% phosphoric acid or vice versa, about 20% sulfuric acid and about 80% phosphoric acid or vice versa, about 30% sulfuric acid and about 70% phosphoric acid or vice versa, about 40% sulfuric acid and about 60% phosphoric acid or vice versa, or about 50% sulfuric acid and about 50% phosphoric acid.

The biomass can be exposed to the pH adjusting agent for a time from about 1 minute to about 240 minutes, from about 3 minutes to about 180 minutes, from about 5 minutes to about 120 minutes from about 5 minutes to about 60 minutes, from about 10 minutes to about 30 minutes, from about 10 minutes to about 20 minutes, or for up to any time within the specified ranges. In other words, as non-limiting examples, the biomass may be exposed to the pH adjusting agent for a time up to about 1 minute, up to about 3 minutes, up to about 5 minutes, up to about 10 minutes, up to about 20 minutes, up to about 30 minutes, up to about 45 minutes, up to about 60 minutes, up to about 90 minutes, up to about 120 minutes, up to about 180 minutes, or up to about 240 minutes.

The conditioning can further include exposure to heat to accelerate the liberation of cell products. Included within the scope of exposure to heat, as used herein, is exposure to ambient temperatures or higher. In certain embodiments, the hydrated biomass can be subjected to temperature ranges of about 25° C. to about 200° C., of about 45° C. to about 150° C., of about 55° C. to about 140° C., or of about 60° C. to about 130° C. Preferably, the temperature is 120° C., but depending on the source of algae material, the species of the algae material, the differences between batches, and the inherent variability of algae, this number can be varied. More generally, temperature and pH can be varied to vary end fraction production. In other words, modifying conditions can give modified fraction yields. The inventive system allows for variance of temperature, pressure, or incubation time in order to decrease or increase fractions derived. The effect of various temperatures on the fractionation is shown in Example 4.

The permeability conditioning step can further include partial or complete enzymatic hydrolysis. Enzymes are advantaged as a specific biocatalysts and can operate under mild reaction conditions. The enzymatic hydrolysis utilizes algal biomass to first reduce the size of the polysaccharides to make it easy to release of lipids. Furthermore, the enzymes are substrate specific; as such they can hydrolyze algal cell wall effectively. Among others, cellulase, hemicellulases, lipase and algaenan conversion enzymes are important enzymes for the hydrolysis of cell wall polysaccharides into simple sugars. Cellulases are primary enzymatic sources for hydrolysis of cellulose into sugar. In general, multicomponents of three different enzymes (endocellulase, cellobiohydrolase and β-glucosidases) synergistically interplay to complete hydrolysis of cellulose. Hemicellulases, similar to other enzymes that hydrolyze xylanase polysaccharides, are multi-domain proteins. Based on the amino acid or nucleic acid sequence of their catalytic modules, hemicellulases are glycoside hydrolases, which hydrolyze glycosidic bonds to carbohydrate esterases, which hydrolyze ester linkages of acetate or ferulic acid side groups. Xylan is the most abundant hemicellulose; xylanases are among the major hemicellulases that hydrolyze the β-1,4 bond in the xylan backbone yielding short xylose-oligomers that are further hydrolyzed by β-xylosidase into single xylose units.

Alternatively, the conditioning step can include suspending the biomass solely in carbon dioxide and water. The carbon dioxide can be present in various phases, and preferably is in a liquid phase or supercritical phase. The chamber used to contain such a combination of components must be adapted to the temperatures and pressures required.

The biomass can be exposed to heat for a time of from about 1 minute to about 240 minutes, from about 3 minutes to about 180 minutes, from about 5 minutes to about 120 minutes from about 5 minutes to about 60 minutes, from about 10 minutes to about 30 minutes, from about 10 minutes to about 20 minutes, or for up to any time within the specified ranges. In other words, as non-limiting examples, the biomass can be exposed to heat for a time up to about 1 minute, up to about 3 minutes, up to about 5 minutes, up to about 10 minutes, up to about 20 minutes, up to about 30 minutes, up to about 45 minutes, up to about 60 minutes, up to about 90 minutes, up to about 120 minutes, up to about 180 minutes, or up to about 240 minutes. The speed of fractionation of cellular components can be optimized by adjusting the pH and temperature.

Conditioning of the hydrated biomass (or the algal paste where used) to create a disordered cellular material, can also be performed by any combination of two or more means, in any order or combinations. Thus, for example, the hydrated biomass can be conditioned by exposure, in any order, to a pH adjusting agent and to heat, enzyme and carbon dioxide in accordance with any combination of the embodiments presented above. In a non-limiting example, the hydrated biomass can be conditioned, therefore, in any order, by combining the biomass with a single target enzyme followed by a pH adjusting agent and subjecting the biomass to a temperature of about 25° C. to about 200° C. for a time of from about 5 minutes to about 120 minutes.

In certain embodiments, it is preferred that the conditioning agent(s) utilized be carried through into subsequent steps of the methods of the present invention. In a non-limiting example, where an acid or a mixture of acids is used to condition the cells, it is preferred that the disordered cellular material is not neutralized and/or remains acidic throughout the fractionation process.

In a certain embodiment, biomass conditioning can be improved by subjecting algae cells to low voltage pulse electric fields to increase the porosity of algae cells to enhance mass transfer of algae constituents such as lipids. Biomass is subjected to repeated low voltage pulse electrical fields by flowing across electrical conductors to partially or fully open pores in algae cell walls and membranes to release algae constituents such as lipids. These electrical pulses can depend upon electrical conductivity of biomass, dilution, voltage, current, pulse duration, pulse frequency, and pulse electric field contactor geometry. These pulses can be in the range of microseconds to milliseconds. The voltage of pulsed electric field can be in the range of 1 to 150 volts, and more preferably at 2 to 15 volts.

In a certain embodiment, biomass conditioning can be improved by subjecting algae cells to high voltage pulse electric field to improve the porosity of algae cells to enhance mass transfer of algae constituents as demonstrated in Example 17. Biomass is subjected to repeated intense electrical flux by flowing across a series of electrical conductors to partially or fully burst open algae cell walls and membranes to release algae constituents such as lipids. These electrical pulses can depend upon electrical conductivity of biomass, dilution, voltage, current, pulse duration, pulse frequency, and pulse electric field contactor geometry. These pulses can be in the range of microseconds to milliseconds. The voltage of pulsed electric field can be in the range of 150 to 9000 volts, and more preferably at 1500 to 3000 volts.

Following the conditioning step, the intimate contacting step is performed. The intimate contacting step is preferably performed with a single non-polar (such as hexane) or mixture of polarity (such as hexane plus ethanol) organic solvents. The solvents allow for fractionation of hydrophobic and non-polar components such as lipids from the biomass cells into the solvents. Examples 5-7 also describe various solvents.

The organic solvent can be any non-polar solvent as known in the art in which the lipid fractions of the biomass are soluble. In certain embodiments the organic solvent is a petroleum distillate. Specific non-polar solvents that can be used with the invention include, but are not limited to, carbon tetrachloride, chloroform, cyclohexane, 1,2-dichloroethane, dichloromethane, diethyl ether, dimethyl formamide, ethyl acetate, butane isomers, heptane isomers, hexane isomers, octane isomers, nonane isomers, decane isomers, methyl-tert-butyl ether, pentane isomers, toluene, hexane, heptene, octane, nonene, decene, mineral spirits (up to C12) and 2,2,4-trimethylpentane. Preferably, the non-polar solvent is selected from the group consisting of hexane, hexane isomers, heptane isomers, or a mixture thereof. More preferably, the non-polar solvent is hexane, isohexane, or neohexane.

In certain embodiments, the non-polar solvent comprises at least 5% by weight, at least about 6% by weight, at least about 7% by weight, at least about 8% by weight, at least about 9% by weight, at least about 10% by weight, at least about 15% by weight, at least about 20% by weight, at least about 25% by weight, at least about 30% by weight, and least about 35% by weight, at least about 40% by weight, at least about 45% by weight or at least about 50% by weight of the biomass-solvent mixture. In certain embodiments, the non-polar solvent comprises less than about 80% by weight, less than about 70% by weight, less than about 60% by weight, less than about 50% by weight, less than about 40% by weight, less than about 30% by weight, less than about 25% by weight, less than about 20% by weight, or less than about 10% by weight of the biomass-solvent mixture. Additionally, it will be understood by one of skill in the art that the weight % of the non-polar solvent may be within inclusive ranges of the limits recited above. In certain non-limiting examples, the non-polar solvent may comprise from about 6% to about 80% by weight, from about 10% to about 70% by weight, from about 20% to about 60% by weight, from about 10% to about 40%, from about 20% to about 40% by weight, or from about 25% to about 35% by weight of the biomass-solvent mixture.

Furthermore, it has been found that an optimal yield of cell metabolites is dependent on the relative amounts of polar to non-polar solvent used in the methods of the present invention. Optimal conditions may be readily derived by one of skill in the art in view of the teachings contained herein. Preferably, the non-polar solvent comprises from about 10% to about 40% by weight of the biomass-solvent mixture.

As a specific example, the ratio of biomass:water:hexane can be 1:15:15 to provide a higher yield of lipids, as demonstrated in Example 5. Alternatively, the ratio can be 1:6:5 to provide a high yield of lipids during a large scale process when the amount of water and hexane need to be conserved to keep operating costs down.

The polar solvent can include a mixture of water along with the solvent. Other solvents can be used or combinations of solvents such as hexane and methanol, or hexane, ethanol, and methanol. Preferably, the biomass solution is at 80° C. at the time the solvent is added, but other temperatures can also be used such as about 60° C. to 120° C. Any other suitable solvent or combination can be used. Other polar solvents include, but are not limited to, low molecular weight aldehydes, ketones (such as acetone), fatty acids, alcohols having typically fewer than 6 carbon chains such as methanol, ethanol, and propanols, and formic, acetic and propionic acids. Additionally, polar solvents can include amphipathic solvents, which can also be used in accordance with the invention as a non-polar solvent. Specific polar solvents and amphipathic solvents known in the art are included within the scope of the invention and can be readily selected by one of skill in the art. In a preferred embodiment, the non-solid portion of the algal paste comprises water. The water can contain additives, including but not limited to salts (including but not limited to sodium chloride and ammonium sulfate), buffers (including but not limited to HEPES, TRIS, MES, ammonium bicarbonate, and ammonium acetate), detergents (including but not limited to SDS, cholate, C16TAB, Triton X, and Tween) or chaotropic agents (including but not limited to urea and guanidinium chloride), and enzyme inhibitors (including but not limited to protease inhibitors and DNAase inhibitors). Where the non-solid portion of the paste comprises water, the salt concentration may range from 0 up to and including about 10% by weight. In certain embodiments, the salt concentration may be about 1%, about 2%, about 3%, about 4%, about 5%, about 6%, about 7%, about 8%, about 9% or about 10%, or within a range of about 0-5%, about 5-10%, about 1-9%, about 2-8%, or about 3-7%.

The disordered biomass and solvent mixture is then subjected to a contacting process for a time sufficient to form a multi-phase suspension, or in certain embodiments, for a time and within a device sufficient to force intimate, proximate, and repetitive contact of the biomass and the polar and non-polar solvents to effectuate metabolite fractionation. Essentially, the contacting provides a liquid/liquid extraction serving to solubilize the non-polar solvent soluble compounds such as lipids in the non-polar solvent and retain the polar hydrophilic or miscible compounds with the water. The lipids or non-polar solvent soluble compounds are then retained in the solvent.

It should be understood that the compounds in the non-polar solvent solution can be polar or non-polar, and that they remain in this solution because of their lipid character and hydrophobic characteristic. The proteins, carbohydrates, and water miscible compounds are retained in the water phase (polar solvent) and are hydrophilic, i.e. water-soluble. In other words, compounds can be separated based on any of these characteristics. Proteins are liberated and some are degraded to short peptides and amino acids. The complex carbohydrates are in great part liberated from the cell mass to partition by way of water-solubilization and degraded by hydrolysis to form simple sugars. This provides many advantages in addition to solubility in water, such as ease of conversion to fuel sources by methods well known in the industry. While the solvent is preferably added after the conditioning step, the solvent can also be added at the same time as conditioning, to simultaneously liberate and extract both the water soluble and solvent soluble cellular components.

Essentially, during this step, the now permeable algae cells are intimately contacted with the solvents. The effective goal of the intimate contacting step is to wash out or flush cells of the products that are desired to be fractionated into the solvents.

The biomass-solvent mixture is subjected to contacting for a time sufficient to form a multi-phase suspension comprising a non-polar (hydrophobic) phase, otherwise known herein as the non-polar solvent solution, containing lipids and a polar (hydrophilic) phase, otherwise known herein as the water soluble solution, containing biomass and cellular debris. This can be accomplished by using a gear pump, cavitation, and/or shock waves. Preferably, the biomass-solvent mixture is subjected to the contacting step immediately after the disordered cellular material is combined with a solvent blend comprising a polar and an non-polar solvent (or with a non-polar solvent), or the solvent blend (or non-polar solvent) is added to the disordered cellular material concurrently with the application of contacting. It should be understood that the contacting process is not breaking the biomass cells, but rather agitating and mixing the cells as well as forcing the solvent phase into intimate contact with the conditioned biomass polar phase without forming an emulsion.

Subjecting the biomass-solvent mixture to sufficient intimate contacting can be achieved by any means known in the art, particularly mechanical or electromagnetic means including, but not limited to, mechanical pumping, homogenization (including but not limited to use of a colloid homogenizer, a rotor/stator homogenizer, a Dounce homogenizer, a Potter homogenizer, etc.), sonicating, vortexing, cavitation, shearing, grinding, milling, shaking, mixing, blending, hammering, or any combination thereof. In certain embodiments, the biomass-solvent mixture is passed through a homogenizer for a time sufficient to form a multi-phase suspension, or in certain embodiments, for a time sufficient to force intimate, proximate, and repetitive contact of the biomass and the polar and non-polar solvents to effectuate fractionation. The biomass-solvent mixture can be homogenized in batch or in continuous-mode.

The optimal time for subjecting the biomass-solvent to contacting will depend on the specific solvents and conditions utilized and can be readily ascertained by one of skill in the art in view of the teachings herein. In certain embodiments, the biomass-solvent mixture is exposed to contacting for a period of time from about 3 seconds to about 120 minutes. In other embodiments, the biomass-solvent mixture is exposed to contacting for a time from about 30 seconds to about 90 minutes, for a time from about 1 minute to about 60 minutes, for a time from about 1 minute to about 30 minutes, for a time from about 1 minute to about 20 minutes, for a time from about 5 minutes to about 20 minutes, for a time from about 5 minutes to about 15 minutes, or for a time from about 10 minutes to about 15 minutes.

In accordance with the invention, application of a contacting process to the biomass-solvent mixture results in a multi-phase suspension comprising a non-polar phase (non-polar solvent solution) comprising fractionated lipids and a polar phase (polar biomass solution) comprising fractionated biomass. In certain embodiments, the suspension can also comprise solid, non-soluble residual biomass.

An alternative type of intimate contacting process is pressure pulsation utilizing a pump system. Such pumps rapidly compress and release, forcing the solvent to flush in and out of the cells, creating a dynamic flushing effect. This hydrodynamic effect results in greater efficiency of solvent washing of the intracellular components. It should be noted that high shear mixing between the blades of the mixer also creates local pressure pulsation to derive a similar effect.

Another method of intimate contact is to run the fluids through a charged zone of alternating positive and negative pulses. This electro-hydrodynamic process results in better mass transfer.

In a certain embodiment, pulsing electric fields can be used to increase intimate contact between biomass and solvent. The hydrated biomass and non-polar phase can be subjected electrical pulses to reduce the size of droplets of one liquid phase into another. Such a shattering of droplets will increase dispersion of one liquid phase into another and will increase mass transfer of algae cell constituents such as lipids from algae cells to solvents. The electrical pulses may depend upon electrical conductivity of biomass, solvent, dilution, voltage, current, pulse duration and pulse frequency and pulse electric field contactor geometry.

Subsequent to the intimately contacting step, the partitioning step separates the water-soluble aqueous phase (polar biomass solution) and the non-polar solvent solution. An interface phase is also created between the polar biomass solution and the non-polar solvent solution that contains the debris of microalgae cells and insoluble proteins and carbohydrates, as well as glycolipids, referred to above as residual biomass. The partitioning step can be accomplished according to means known in the art. For example, the solution can be manipulated to enable simple decantation. Mechanical weight separation such as centrifugation can also be performed, as well as variation in pressure, ultrasonification, heating, or adding to the multi-phase suspension an oil-water de-emulsifying agent. As used in this context, "centrifugation" refers to the use of any device or means that employs centrifugal force. In certain embodiments, the non-polar phase may be isolated by a combination of means. Thus, for example and without intending to be so limited, the non-polar phase may be isolated by subjecting the multi-phase suspension to heat and subsequently to centrifugation. Alternative methods for isolating the non-polar phase not specifically mentioned herein can be readily devised by one of skill in the art.

In certain embodiments, the non-polar solvent solution is isolated by adding an oil-water de-emulsifying agent. Non-limiting examples of the de-emulsifying agent that may be used with the invention include fatty acids, fatty acid esters, aromatic naphtha, heavy aromatic naphtha, naphtha and oxyalkylated resin, organic sulfonic acid, aliphatic hydrocarbon and oxyalkylated resin, oxyalkylate blend, dioctyle sodium sulfo-succinate, and ethoxylated nonylphenol and potassium acetate.

In certain embodiments, the disordered biomass non-polar solvent solution is partitioned by heating the multi-phase suspension. The multi-phase suspension can be subjected to a temperature of about 25° C. to about 200° C., of about 55° C. to about 180° C., or of about 70° C. to about 170° C. The multi-phase suspension can be exposed to heat for a time of from about 1 minute to about 240 minutes, from about 3 minutes to about 180 minutes, from about 5 minutes to about 120 minutes from about 5 minutes to about 60 minutes, from about 10 minutes to about 30 minutes, from about 10 minutes to about 20 minutes, or for up to any time within the specified ranges. In other words, as non-limiting examples, the biomass can be exposed to heat for a time up to about 1 minute, up to about 3 minutes, up to about 5 minutes, up to about 10 minutes, up to about 20 minutes, up to about 30 minutes, up to about 45 minutes, up to about 60 minutes, up to about 90 minutes, up to about 120 minutes, up to about 180 minutes, or up to about 240 minutes.

Although the system of the present invention can be open or closed, preferably the system is closed to recollect volatiles released, and to prevent solvents and water from boiling off at higher temperatures, such as over 100° C.

In a certain embodiment, pulse electric fields and electrostatic forces can be applied across a mixture of biomass and solvents to expedite the separation of polar and non-polar phases. This improvement will enhance algae cell constituent recovery. The electrical pulses may depend upon electrical conductivity of biomass, solvent, dilution, voltage, current, pulse duration and pulse frequency and pulse electric field contactor geometry.

After the phases have been partitioned, each phase can be fractionated and further processed separately to isolate the desired products. Previous methods do not fractionate the cell products, but merely serve to isolate key extracts leaving the residual mass comingled and otherwise limiting application and additional product conversion. The present invention is able to obtain valuable products apart from the lipids by using fractionation. After recovery of products from the polar biomass solution and the non-polar solvent solution, the products can be further refined.

The non-polar solvent solution contains products which include terpenoids such as sterols and carotenoids; chlorophyll, phospholipids, glycolipids, sphingolipids, triacylglycerols, diacylglycerols, monoacylglycerols, fatty acids, decarboxylated fatty acid hydrocarbon chains, methyl esters of the fatty acids, other lipid products, alkyl aromatics and hydrocarbon chains. It should be noted that methyl esters of the fatty acids are produced by the invention without the addition of methanol during processing. Small amounts of free methanol can be observed within the non-polar solvent solution which is generated by the invention.

Extracted triacylglycerols, diacylglycerols, monoacylglycerols, and long chain fatty acids ($C_{14}$-$C_{24}$) from the distillation can then undergo a transesterification step (for tri-, di-, or monoacylglycerols) or an esterification step (for free fatty acids) by adding ethanol or methanol and catalyst. These lipids including monoacylglycerols, diacylglycerols, triacylglycerols, and long chain fatty acids ($C_{14}$-$C_{24}$) consist of the majority of the lipid components of microalgae, all of which cannot be directly used as fuel. The transesterification of acylglycerols and esterification of fatty acids with methanol or ethanol are required to generate long chain alkyl esters as biodiesel. Upon a refined oil phase separation, the final algae oil products including hydrocarbons as direct gasoline alternative, biodiesel, and high value lipids are produced. The phosphorous and polylipids can be converted into diglycerides and phosphocholine. The triglycerides can be converted into glycerin and FFA (free fatty acid). Additionally, astaxanthins can be extracted for use in fish feed industry, antioxidants can be extracted for use in nutraceuticals, and triglycerides and/or fatty acid esters can be further purified to make high valued omega-3 food additive products.

Figure 2:
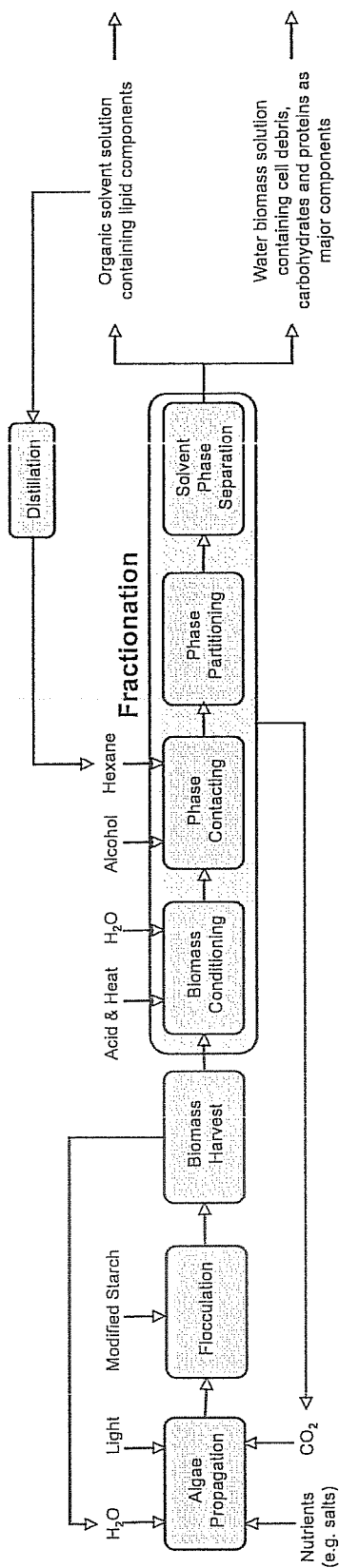
FIG. 2 is a flow diagram of the steps of the fractionation of the algae biomass.

The organic solvent soluble compounds can be isolated from the non-polar solvent solution by means known in the art, including but not limited to conventional distillation, extractive or azeotropic distillation, evaporation, selective absorption (such as chromatography), centrifugation, membrane filtration, or filtration. Where the lipids are recovered by distillation of the non-polar solvent solution, the distillation can be performed at modest temperatures of, for example 40° C.-120° C. at ambient pressures or under vacuum. One of skill in the art can readily ascertain optimal distillation conditions. With solvent distillation, the solvent can be recycled back to the mixing step as shown in FIG. 2.

The lipids so isolated from the non-polar solvent solution can be used directly, or they can be further processed in accordance with their intended use. For example the lipid fraction can be processed for decoloring. The dark green pigmentation of microalgal oil, as an example, may pose downstream processing difficulties for biodiesel producers where color is a fuel sales and performance criteria. Decolorization could include activated carbon treatment, microfiltration, etc. The lipids can also be winterized (i.e. chilled to precipitate out higher melting point materials and suspended solids).

Figure 5:
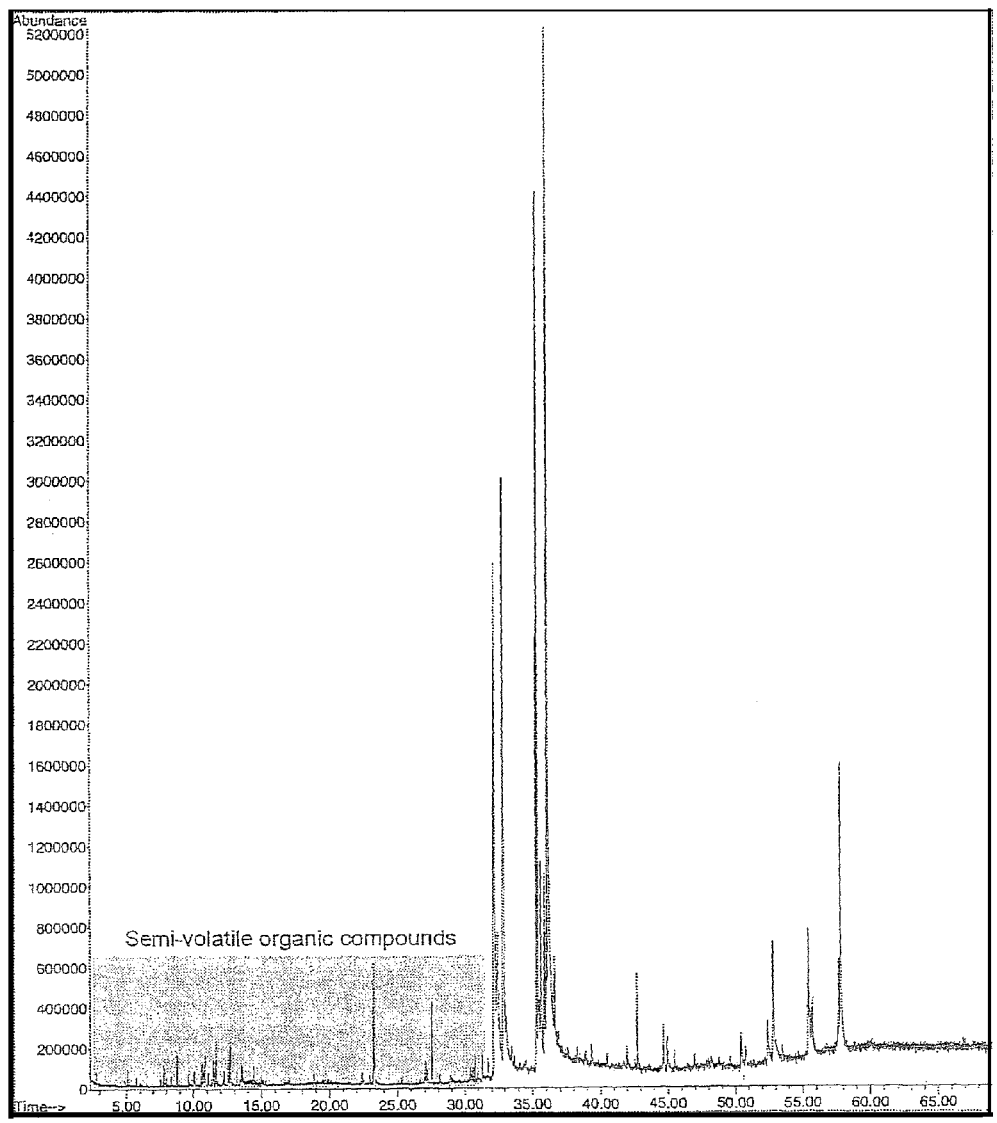
FIG. 5 is the result of the GC/MS profile of the fractionated non-polar components.

In some cases, the method further provides for isolation of naturally occurring hydrocarbons and catalyzing the formation of valuable hydrocarbons derivatives such as semi-volatile and other organic compounds. The present invention provides for separation and formation of organic compounds selected from a group not limited to aromatic hydrocarbons, substituted benzene derivatives, and branched and straight chain alkanes and alkenes such as but not limited to: toluene; xlyene; styrene; trimethyl-benzene; 2-ethyl-toluene; 1-methyl-3-propopyl-benzene; tetramethyl-benzene; methyl-propenyl-benzene; naphthalene; alkyl substituted naphthalene; heptadecane; heptadecene; isoprenoid fragments such as: 2,2,6,6-tetramethylheptane; 2,5,-dimethylheptane; 2,4,6-trimethylheptane; 3,3-dimethyl octane; 2,2,3-trimethylhexane; 2,2,6,6-tetramethylheptane; 2,2,3,4-tetramethylpentane; 2,2-dimethyldecane; 2,2,4,6,6-pentamethylheptane; 2,4,4-trimethylhexane; 4-methyldecene; 4-methyldecane; 3,6-dimethyloctane; 2,6-dimethylundecane; 2,2-dimethylheptane; 2,6,10-trimethyldodecane; 5-ethyl-2,2,3-trimethylheptane; 2,5,6-trimethyldecane; 2,6,11-trimethyldodecane and isomers of the afore listed compounds. Not intended to be bound by a particularly theory, these hydrocarbon compounds are degradation products from algae hydrocarbon compounds and other organic compounds such as α and β-carotene, astaxanthin, lutein, zeaxanthin, and lycopene which are unique to algae and can be found in every species, and act to shade algae from sunlight. Different amounts of semi-volatiles can be found in algae based on their treatment before harvesting, as well as process conditions of pH, temperature, and solvent ratios used in the steps of the present invention. These semi-volatiles and carotenoids can be used as a component in jet fuel. FIG. 5 shows semi-volatile compounds in relation to other extracted nonpolar compounds.

In some embodiments, the present invention provides for fractionation of valuable aqueous soluble biological metabolites while catalyzing the reaction of metabolites to higher value compounds. In some cases, the permeability conditioning step serves to improve cell wall permeability and breakdown the complex polar compounds into reduced or substituted higher value compounds. Temperature and pH play a key role in fractionating the polar compounds and catalyzing the formation of derivative products. Specifically, the present invention provides for reduction of carbohydrates into simple sugars and breakdown of proteins to short peptides and amino acids.

The water-soluble phase, also referred to as the polar biomass solution, is uniquely concentrated with amino acids, soluble proteins, peptides, fiber, nutrients, soluble carbohydrates (monosaccharides, disaccharides, oligosaccharides, and polysaccharides), simple organic acids and alcohols, phosphate, and phosphocholine. The amino acids can include, but are not limited to, tryptophan, cysteine, methionine, asparagine, threonine, serine, glutamine, alanine, proline, glycine, valine, isoleucine, leucine, tyrosine, phenylalanine, lysine, histidine, and arginine. The carbohydrates can include, but are not limited to, cellobiose, glucose, xylose, galactose, arabinose, and mannose. The simple organic acids and alcohols can include, but are not limited to, malic acid, pyruvic acid, succinic acid, lactic acid, formic acid, fumaric acid, acetic acid, acetoin, glycerol, methanol, and ethanol. The residual cellular debris contained within the polar biomass solution is rich in protein and fiber and can be separated from the aqueous solution and compounds by traditional liquid/solid separation techniques.

In some embodiments, the present invention provides for fractionation of valuable biological metabolites and while catalyzing the reaction of metabolites to higher value compounds. In some embodiments, the lipid compounds are catalyzed to form fatty esters. Instead of performing a transesterification step after partitioning as described above, transesterification is performed before partitioning. This process is accomplished by permeability conditioning algae biomass suspended in water by acid addition to form a pH adjusted solution, mixing the pH adjusted solution with alcohol (e.g. ethanol or methanol) and simultaneously transesterifying acylglycerols and esterifying free fatty acids, partitioning the solution, obtaining a polar biomass solution and an non-polar solvent solution, and recovering cell products from the non-polar solvent solution and polar biomass solution.

In presence or absence of exogenous catalyst, the mixing step also serves to simultaneously transesterify acylglycerols or esterify free fatty acids formed by the acid hydrolysis of conditioning step. Herein, the acid serves as a catalyst for transesterfication, esterification, and hydrolysis reactions. This reaction is achievable at reasonable temperatures and pressures. In the right processing conditions, these reactions produce methyl or ethyl esters or biodiesel directly or integral with the extraction. Not all fatty acids are transesterified or esterified via this pathway depending on operating conditions as well as the algae biomass fatty acid profile. The esters and remaining lipids are organic solvent soluble compounds and retained in the solvent. The proteins and carbohydrates, and water miscible compounds are retained in the water phase.

The partitioning step as in the above method separates the water-soluble aqueous phase and the non-polar solvent soluble phase and is accomplished by means known in the art. For example, the solution can be manipulated to enable simple decantation. Mechanical weight separation such as centrifugation can also be performed.

After the phases have been partitioned, each phase can be further processed separately to obtain the desired products. The non-polar solvent soluble compounds including the esters can be isolated from the non-polar solvent soluble phase by means known in the art, such as, but not limited to, distillation. The polar biomass solution can be further processed as described in the method above. The alcohol/solvent/lipid mixture is fractionated by distillation or other separation methods to enable collection of the polar neutral lipids, fatty acid ethyl esters, and solvent soluble polar lipids. This is generally done in two steps to first remove the solvent then separate any residual water from the lipid. The solvents are reused and can be recycled into the process. The organic mixture is further purified by downstream uses, such as biodiesel, TGs, glycerine, polar neutral lipids, etc.

Figure 3:
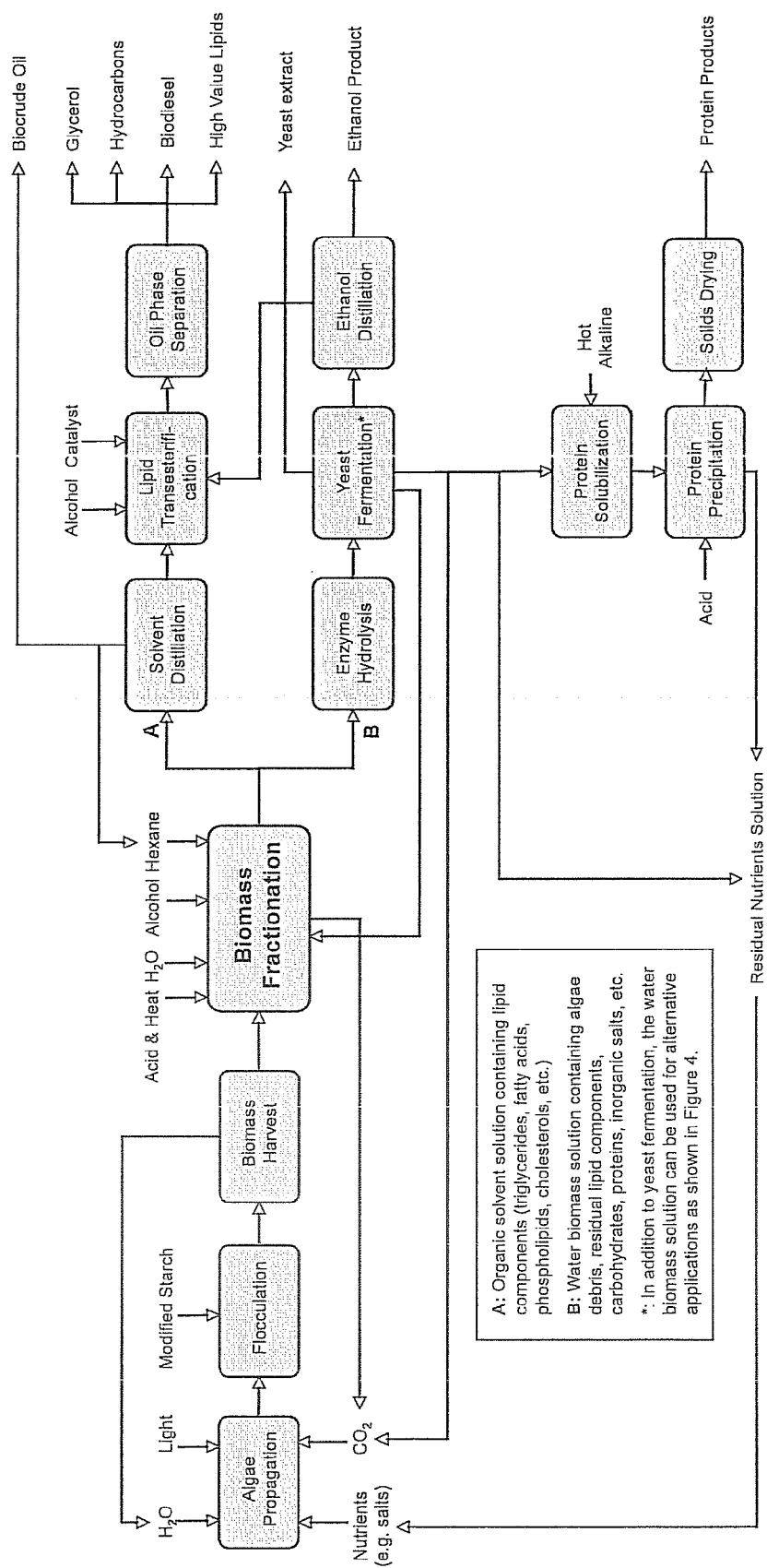
FIG. 3 is a flow diagram of the steps of the large-scale process of the present invention.
Figure 4:
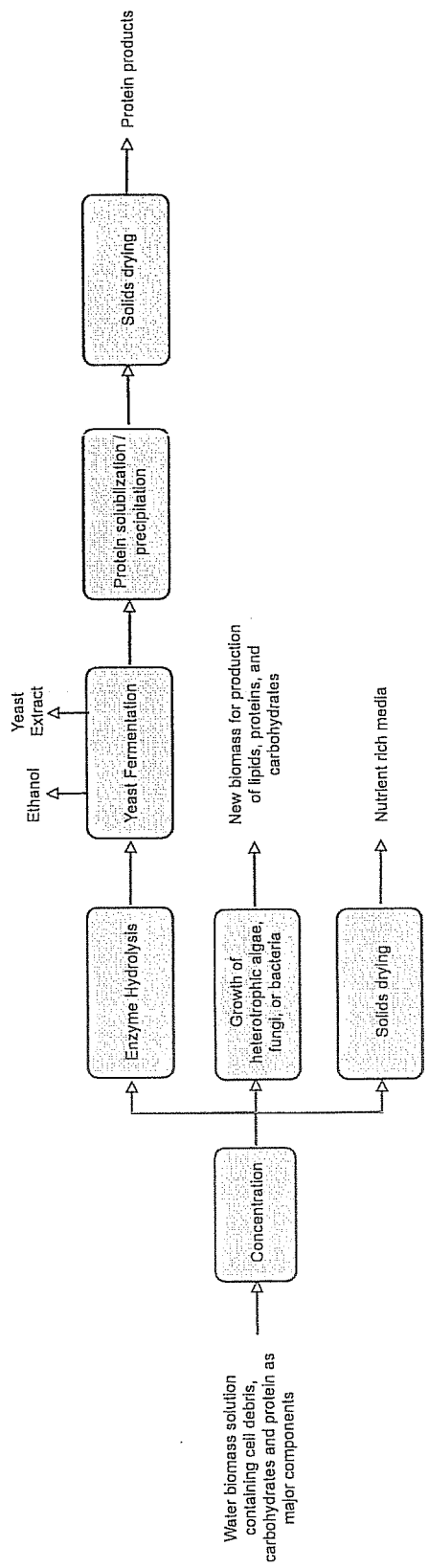
FIG. 4 is a flow diagram of alternative steps of polar biomass solution processing.

In some embodiments, the polar biomass solution serves as a rich aggregate solution suitable as a substrate for additional product or liquid fuel creation by way of heterotrophic growth of microalgae, or digestive microbiology such as direct yeast fermentation as shown in FIGS. 3 and 4. The solution is a unique mixture concentrated with desired nutrients such as simple sugars, inorganic salts, and metabolites such as amino acids and phosphate to foster rapid propagation of yeast fermentation or heterotrophic algae production. If necessary, this base media can be supplemented with custom blends of additional organic carbons and dissolved inorganic nutrients such as additional carbohydrates such as fructose or additional nutrients such as calcium chloride, potassium phosphate, dissolved amino acids, dissolved organic and inorganic nitrogen.

In another aspect, the present invention further provides for a method of enzymatic hydrolysis followed by yeast fermentation of the aqueous biomass solution to generate alcohol, carbon dioxide and a protein concentrate. The method comprises (a) concentrating the valuable compounds dissolved and suspended within the polar biomass solution within the aqueous conditioning agent by recycling loops within the process, counter current processing or means known in the art, (b) providing for liquification and saccrification of residual biomass solids by enzymatic hydrolysis using any suitable combination of hydrolase, and supplementing if necessary the aqueous solution with custom blends of additional fixed carbon and dissolved inorganic nutrients, and (c) digesting the concentrated blended solution with a select strain of yeast or a combination of more than one yeast strains in a fermentation process utilizing the sugars, amino acids, algae extract, and nutrients to propagate and generate alcohol and carbon dioxide.

In some cases, enzymatic hydrolysis can be performed on the polar biomass solution before fermentation using any suitable hydrolase, including, but not limited to, commercial hydrolases (Novozymes) including the cellulase complex (NS50013), β-glucanase (NS50012), and β-glucosidase (NS50010). As Example 12 shows, using enzymatic hydrolysis can increase the yield of glucose, cellobiose, galactose, and mannose. An increased yield of these products provides for a better growth media composition as well as a better composition for subsequent fermentation.

In another aspect, the present invention is directed to utilization of the aqueous biomass solution as a base substrate or biological growth media to support mixotrophic, heterotrophic, or chemautrophic biological production. The method comprises (a) concentrating the valuable compounds dissolved and suspended within the polar biomass solution within the aqueous conditioning agent by recycling loops within the process, counter current processing or means known in the art such as evaporation or membrane separation, (b) supplementing the aqueous solution with custom blends of additional fixed carbons and dissolved inorganic nutrients, and (c) inoculating with a organism most suitable to the desired product production such as heterotrophic algae or fungus, mixotrophic algae such as *Chlorella* or *Dunelliala* either in a dedicated production system or as a lipid fattening operations.

In the above described post-lipid-extraction steps, it is preferred that the mixotroph, heterotroph, or chemautotroph do not consume any residual fatty acids such that any residual fatty acids could be once again extracted or otherwise separated much like corn stillage or corn oil removal. It is also preferred that the selected mixotroph, heterotroph, or chemautotroph serve to metabolically convert the residual organic phosphorous to soluble inorganic phosphorous for purposes of application to the exogenous production platform as a key nutrient. Key to this novel process was a discovery that the biological digestion greatly reduces or eliminates the solid cell structure fraction and enables nearly complete soluble metabolites. That is, most proteins are now broken down into amino acids or soluble polypeptides. Carbohydrates are consumed whether from the original hydrolysis or from the digestion process.

In another aspect, the present invention further provides for a method of yeast fermentation using a yeast, bacteria, algae, or fungi of the aqueous biomass solution to generate alcohol, carbon dioxide and a protein concentrate. The method comprises (a) concentrating of the valuable compounds dissolved and suspended within the polar biomass solution within the aqueous conditioning agent by recycling loops within the process, counter current processing or means known in the art, (b) supplementing the aqueous solution with custom blends of additional fixed carbon and dissolved inorganic nutrients, and (c) then digesting the concentrated blended solution with a select strain of yeast or a combination of more than one yeast strains in a fermentation process utilizing the sugars, amino acids, and nutrients to propagate and generate alcohol and carbon dioxide.

In another aspect of the invention, there is beneficial use in using the residual acid produced from fractionation platform as a saccrification and liquification solution serving to digest and reduce additional carbohydrates being supplemented to the base media as described above.

By using yeasts that can process every component, a higher yield of alcohol can be obtained, as shown in Example 15. Various types and strains of yeast can be used depending on the different types of carbohydrates and sugars that are present in the polar biomass solution.

In some embodiments, the process of alcohol fermentation of the fractionated aqueous metabolites, the alcohol and water solution can then be purified to remove the solids and reused as a water alcohol mixture within the fractionation process. In some cases, the alcohol can be used as the extraction solvent as well as an esterifying solvent. This accommodates process efficiency whereby the necessity to remove residual solvent from the water is minimized as the fermentation process is generating alcohol, and therefore, only one alcohol distillation is required post fermentation. The carbon dioxide can be concentrated and reused in the algae biomass production in another recycle stream. The method of the present invention is further unique in that purified water can be obtained to recycle back to any step of the process, and preferably algae cultivation, reducing the need for wastewater treatment.

In another embodiment, a method is provided that specifically combines the esterification method above with the production of alcohol. The steps of the esterification method above are performed to obtain the polar biomass solution and non-polar solvent solution. At this point, the polar biomass solution can optionally be returned for additional processing with the alcohol remaining or further processed in a way to remove alcohol sufficiently to enable adequate fermentation of the carbohydrates.

In another embodiment, the post fermentation fraction can be further processed to affect additional metabolite fractionation, as further described in Example 15. In some cases, the post fermentation liqueur can be processed by repeating the present fractionation invention as described in Example 12.

In another embodiment, the post fermentation resulting solution tends to contain only small amounts of suspended solids and a high concentration of dissolved or miscible suspended compounds. This is a novel condition that enables further access and purification of the proteins, amino acids, and lipids. In this case, the additional metabolite liberation has been observed and the liqueur solution can be further processed to affect additional metabolite fractionation by more traditional means of partitioning and isolation such as centrifugation or filtration to affect separations.

In another embodiment, the post enzymatic hydrolyzed resulting solution tends to contain only small amounts of suspended solids and a high concentration of dissolved or miscible suspended compounds. This is a novel condition that enables further access and purification of the proteins, amino acids, and lipids. In this case, the additional metabolite liberation has been observed and the liqueur solution can be further processed to affect additional metabolite fractionation by more traditional means of partitioning and isolation such as centrifugation or filtration to affect separations.

During the yeast fermentation, the distilled alcohol can either be used for production of fuel alcohol or subjected back to the transesterification step above. In addition, the residual yeast cells can be recovered by centrifugation to produce yeast extracts and another byproduct $CO_2$ can be recycled back to algae cultivation areas such as bit not limited to ponds for algae growth. Depending on the amount of the unfractionated lipid components in the post-fermentation fraction, an iterative fractionation can be performed to maximize the yield of algae oil, as shown in Example 15. When lipid components are depleted upon iterative fractionation and carbohydrates are exhausted by yeast fermentation, the high-content proteins can be isolated and purified using traditional alkaline solubilization and acid precipitation. The generated protein products can be used either as additive to livestock and fish feed or for production of higher value products such as amino acids. Alternatively, a solid dry agricultural substrate can be directly added to the lipid and carbohydrate exhausted post-fermentation fraction to make animal feed or provide for an extruded nugget or granules using dried distiller grains, ground corn cobs, milled corn stover, or other dried agricultural substrates. A protein solid or syrup product can be generated that can be fed to animals or used in agricultural formulations for fish or humans.

It should be understood that various aspects of the above-described steps can be altered to derive different products in the non-polar soluble solution and the polar biomass solution. For example, different acids at different pHs can be used in the permeability conditioning step. As shown in Example 10, a lower pH provides higher yields of monosugars. Different solvents can be used in the intimately contacting step. Combinations of different acids and different solvents can be used. Also, the temperatures and pressures described above can be varied in order to customize the output of products in each solution.

In the case of yeast fermentation, the polar biomass solution would not require complete desolventizing such that the alcohol used in fractionation would be consistent with that produced from fermentation such as ethanol or butanol. This serves to reduce integrated or iterative purification. In the case of heterotrophic algae growth or bacteria digestion, the solution would need to be desolventized. The produced biomass would be processed in a side stream or with the phototrophic algae. In the case of alcohol, production of this solvent would serve to feed any solvent consumed in fatty acyl esters conversion in the process such as that little to no external fossil fuel petrochemical consumable is required.

The final water fraction remaining post-fermentation is uniquely concentrated with proteins and amino acids. Concentration and fractionation of these components is well known. For purposes of algae production, the residual high protein water can be digested to capture nutrients such as nitrogen and phosphorous and other micronutrients.

A method can also be performed of fractionating biomass by permeability conditioning biomass suspended in water to form a pH adjusted solution and liberating cell products from within the biomass, intimately contacting the pH adjusted solution with at least one non-polar solvent, and partitioning to obtain a polar biomass solution and an non-polar solvent solution. After partitioning, the following steps are performed: concentrating the polar biomass solution, fermenting the concentrated solution with yeast, and obtaining lipids from unfractionated lipid components in a post-fermentation fraction by repeating the permeability conditioning step, the liberating step, the intimately contacting step, and obtaining steps. Each of these steps have been described above. This method allows for iterative fractionation of lipids to increase the overall yield of lipids.

Various additives can be added to the algae cultivation areas before the permeability conditioning step occurs, or at various steps in the process. For example, the process of the present invention can also include a step of adding modified starch to the harvesting step that is shown in FIG. 2 before permeability conditioning occurs. Currently, flocculants are added to algae cultivation areas in order to aid in collecting the algae as they cause the algae to stick together. However, flocculants are a contaminant in the final products and must be removed. It would therefore be advantageous to use a flocculant that does not contaminate the final products. Modified starch can be added at harvesting, it is easy to fractionate into the polar biomass solution, and it also increases the amount of sugar that is available to yeast in a fermentation/digestion step such that additional sugar is not required to be added or reduced amounts of sugar can be added, reducing operating costs. The modified starches are known in the art and can be prepared as described in U.S. Pat. Nos. 5,928,474; 6,033,525; 6,048,929; 6,699,363.

Also, sugars can be added to derive various alcohol products. Phototropes can be added to increase oil production of the algae. In other words, the algae growth can be manipulated and specific end products can be derived by adding the additives at the front end of the process (algae cultivation) or at various steps as required.

The present invention also provides for a method of operating a renewable and sustainable plant for growing and processing algae. This method is performed by growing algae in cultivation areas, harvesting the algae, permeability conditioning the algae to form a pH adjusted solution and liberating cell products from within the algae, intimately contacting the pH adjusted solution with at least one non-polar solvent, partitioning the solution, obtaining an non-polar solvent solution and a polar biomass solution, obtaining growth media and carbon dioxide from the polar biomass solution, and recycling the carbon dioxide and growth media to the algae pond for renewable and sustainable operation. Each of these steps have been described in detail above. While many different products can be obtained by the polar biomass solution and the non-polar solvent solution, the carbon dioxide and growth media in particular can be used to grow algae, thus reducing cost and creating a manufacturing plant that supports itself.

Essentially, the manufacturing plant is an integrated biorefinery. A biorefinery typically uses biological matter and produces transportation fuels, chemicals, as well as heat and power. The biorefinery can be self-sustaining by using the products derived from the biological matter to heat and power the facility. In the case of the present invention, there are many different products which can be recycled back to the plant for power, processing, as well as feed of the algae as described above.

The present invention also provides a method of fractionating biomass by permeability conditioning biomass suspended in water with a pH adjusted solution to form a conditioned biomass, intimately contacting the conditioned biomass with at least one non-polar solvent, partitioning to obtain an non-polar solvent solution and a polar biomass solution, converting organic phosphorus into inorganic phosphate, and recovering the inorganic phosphate. Each of these steps have been described above, and the phosphorus conversion is also described in Example 13. Obtaining inorganic phosphate is useful for any growth media.

The present invention further provides for a method of fractionating biomass, including the steps of: permeability conditioning biomass suspended in water with a pH adjusted solution to form a conditioned biomass, intimately contacting the conditioned biomass with at least one non-polar solvent, partitioning to obtain an non-polar solvent solution and a polar biomass solution, and obtaining biocrude. Biocrude is a replacement for crude oil made from biomass. Thus the biomass of the present invention can be converted into a useful biofuel. Preferably, the biocrude includes the following compounds: terpenoids such as sterols and carotenoids, chlorophyll, phospholipids, glycolipids, sphingolipids, triacylglycerols, diacylglycerols, monoacylglycerols, fatty acids, decarboxylated fatty acid hydrocarbon chains; methyl, ethyl, propyl, butyl and/or amyl esters of the fatty acids, aromatics, alkyl aromatics, polyaromatics, naphthalene, alkyl substituted naphthalene, linear and branched alkanes, linear and branched alkenes, alcohols such as methanol, ethanol, butanol, and other lipid compounds.

Overall, wet fraction in this invention provides the base framework for chemical reactions and conditioning to affect desirable liberation and access to key biochemical algae compounds to greatly add value and sales revenues to the overall process, thus making it economically viable versus those pursuing the dry algae hexane extraction method.

Isolation of compounds becomes the unique feature of this invention. Preconditioning in a liquid phase allows high lipid concentrations and simultaneously allows the algae to remain in a liquid phase and amenable to further processing using enzymes for saccharification and then microbes for fermentation to biofuels, leaving residual proteins in solution to harvest post-distillation.

In the description of the invention disclosures hereunder, the specific means of implementing a totally wet milling process for algae for compound isolation is given in detail. It applies to a broad range of algae and achieves some of the highest lipid, polysaccharide, protein and sugar yields thus reported in the prior art by integration of the wet process into an Integrated Biorefinery.

The invention is further described in detail by reference to the following experimental examples. These examples are provided for the purpose of illustration only, and are not intended to be limiting unless otherwise specified. Thus, the present invention should in no way be construed as being limited to the following examples, but rather, be construed to encompass any and all variations which become evident as a result of the teaching provided herein.

EXAMPLE 1

Microalgae Biomass Fractionation

Following the invented biomass fractionation process shown in FIG. 1, a selected *Nannochloropsis* sample (the same sample was used in Examples 1, 10, 13, and 16 unless specified, the microalgae samples used in different examples were different from one another) was fractionated into three main fractions (FIG. 2). Upon normalization of the experimental results to "grams of component per 100 grams of dry weight based biomass", 25.9 g of biocrude oil containing lipids, hydrocarbon chains, and semi volatile organic compounds was fractionated into the organic solvent (hexane). The sugars (6.2 g), organic acids (1.5 g), protein products (4.5 g), glycerol (0.6 g), ethanol (1.9 g), phosphate (5.9 g), and unidentified contents (9.1 g), presumably including solubilized $CO_2$, diverse salts, and etc.) were released to aqueous fraction. Although there remained 45.0 g of insoluble materials, a majority of cell (55%) components were fractionated for further alternative utilizations or providing diverse end products upon refinements with known arts (FIGS. 3 and 4). Moreover, the unfractionated biomass can be combined to a new batch of biomass fractionation to exhaust the valuable cell derived products.

EXAMPLE 2

Fractionation of Lipid Components from Microalgae

Fractionating lipids from a *Nannochloropsis* species whose lipid material accounts for approximately 43% of dry weight as an example, a sample of this *Nannochloropsis* sp. (the same sample was used in Examples 2, 6, 7, and 8) biomass containing 18.9% dry weight solids (DWS) was first resuspended in water and the pH was adjusted to about 2.0 by adding 1.3 g of a combination of 50% phosphoric acid and 50% sulfuric acid (TABLE 1) in a 300 ml beaker. The mixture was heated to 60° C. for 15 minutes with agitation.

TABLE 1

| Components | Weight | Parts by weight | Weight % |
| --- | --- | --- | --- |
| Algae as DWS | 9.49 g | 1.00 | 4.54% |
| Water, polar solvent | 118.90 g | 12.53 | 56.83% |
| Hexane, non-polar solvent | 80.83 g | 8.52 | 38.63% |
| Total | 209.22 g | 22.05 | 100% |
| Conditioning acid | 1.3 g | 0.14 | — |

This combination of chemical and mechanical treatment of algae cells generated a population of partially disrupted (~50% cells were disrupted based on microscopic observation) microalgae cells. Surprisingly, these partially damaged cells were proven to be as accessible to the fractionation solvent as the completely disrupted cells regarding the overall production of lipids upon the following hexane fractionation. It is evident that this conditioning and permeability generating method is energy-effective with no cost of fractionation efficiency. The mild acidic condition with mechanical movement might well mimic the stomach conditions of the fishes that use microalgae as their major food resource, representing an optimal conditions to lyse the microalgal cells energy-effectively. Moreover, the acid treatment can benefit the whole process through hydrolysis of triglycerides, diglycerides, and monoglycerides, fatty acyl ester, polysaccharides, and peptide bonds in protein, and neutralization of fatty acids to facilitate the non-polar organic solvent fractionation.

Subsequently, a non-polar solvent, hexane, was added to the sample and the mixture was transferred into a one liter hopper and intensely mixed with a high shear mixer (Homogenizer model # HSM 400DL Manufactured by Ross) for 15 minutes at 40° C. Following the high shear mixing, the mixture was heated to 80° C. for 15 minutes in a 500 ml flask that is connected to a water-cooling reflux condenser for phase partitioning. The phases, once partitioned, were separated by centrifugation within 250 ml centrifuge tubes using an IEC Centra CL3 desktop centrifuge. The lipid containing non-polar (hexane) solution formed a layer above an interface layer containing conditioned microalgae cells and residual insolubles and the lower aqueous layer. The non-polar solution was transferred to a clean flask with a pipette, the hexane was distilled and the lipids were collected. The recovered hexane was added back to the mixture containing the microalgae cells, residual insolubles, and the aqueous solution, and then subjected to the high shear mixing once again to fractionate the remaining lipid components. Similar partitioning and phase separation steps were repeated and the second batch of fractionated lipids was combined to the first fractionation to determine the total yield. As result, a 33% yield (of DWS) of lipids were harvested, accounting for approximately 77% of total lipids of this *Nannochloropsis* species.

EXAMPLE 3 pH Variation in the Fractionation of Lipid Components from Microalgae

Five aliquots of 52.5 g (dry weight) of a *Nannochloropsis* sp. biomass was suspended with 787.5 g of water and the pH was adjusted to 1, 3, 5, and 7 with sulfuric acid. The aqueous suspension was pre-conditioned at 120° C. for 60 minutes with agitation. Then, 787.5 g of hexane was added to afford a fractionation mixture with the biomass:water:hexane ratio of 1:15:15. The lipid fractionation was performed in a positive displacement roller type pump for 30 minutes at 80° C. After fractionation, the aqueous phase and the hexane phase were separated by centrifugation. The lipid components fractionated by hexane was recovered by distillation of hexane. The aqueous biomass solution was fractionated once again by following an identical procedure. The lipids were combined and weighed for calculation of the yields. As shown in TABLE 2, the microalgae lipid fractionation under stronger acidic condition showed a higher yield of fractionated lipids.

TABLE 2

| Pre-conditioning time | Pre-conditioning temperature | pH | Fractionation time | Fractionation temperature | Mix ratio (biomass:water:hexane) | Lipid Yield |
| --- | --- | --- | --- | --- | --- | --- |
| 60 min | 120° C. | 1 | 30 min | 80° C. | 1:15:15 | 25.60% |
| 60 min | 120° C. | 2 | 30 min | 80° C. | 1:15:15 | 21.71% |
| 60 min | 120° C. | 3 | 30 min | 80° C. | 1:15:15 | 18.54% |
| 60 min | 120° C. | 5 | 30 min | 80° C. | 1:15:15 | 14.49% |
| 60 min | 120° C. | 7 | 30 min | 80° C. | 1:15:15 | 12.67% |

EXAMPLE 4

Temperature Variation in the Fractionation of Lipid Components from Microalgae Five aliquots of 85.0 g (dry weight, DW) of a *Nannochloropsis* sp. (the same sample was used in Examples 4 and 5) biomass was suspended with 1,275.0 g of water and the pH was adjusted to 2 with sulfuric acid. The aqueous suspension was pre-conditioned under a number of temperatures ranging from 80 to 150° C. for 60 minutes with agitation. Then, 1,275.0 g of hexane was added to afford an fractionation mixture with the biomass:water:hexane ratio of 1:15:15. The lipid fractionation was performed in a positive displacement roller type pump for 30 minutes at 80° C. After fractionation, the aqueous phase and the hexane phase were separated by centrifugation. The lipid components fractionated by hexane was recovered by distillation of hexane. The aqueous biomass solution was fractionated once again by following an identical procedure. The lipids were combined and weighed for calculation of the yields. As shown in TABLE 3A, the variation of temperature between 80 and 150° C. does not significantly affect the yield of fractionated lipids of this *Nannochloropsis* sample under pH2 treatment.

In addition, five aliquots of 40.1 g (DW) of another *Nannochloropsis* sp. biomass was suspended with 614.7 g of water and the pH was adjusted to 1 with sulfuric acid. The aqueous suspension was pre-conditioned under a number of temperatures ranging from 80 to 130° C. for 60 minutes with agitation. Then, 614.7 g of hexane was added to afford an fractionation mixture with the biomass:water:hexane ratio of 1:15:15 and a similar lipid fractionation was performed as described above. The combined lipids were weighed for calculation of the yields. As shown in TABLE 3B, the higher temperature (e.g. 120 and 130° C.) significantly improved the lipid yield for the selected *Nannochloropsis* sample under pH1 treatment. Thus, the efficiency of the fractionation of lipid components from microalgae biomass is dependent on microalgae species, pH, and temperature. Among tested conditions, however, high temperatures (i.e. 120 or 130° C.) and low pH (i.e. 1 or 2) are preferable.

TABLE 3B

| Pre-conditioning time | Pre-conditioning temperature | pH | Fractionation time | Fractionation temperature | Mix ratio (biomass:water:hexane) | Lipid Yield |
| --- | --- | --- | --- | --- | --- | --- |
| 60 min | 80° C. | 1 | 30 min | 80° C. | 1:15:15 | 26.11% |
| 60 min | 100° C. | 1 | 30 min | 80° C. | 1:15:15 | 25.82% |
| 60 min | 120° C. | 1 | 30 min | 80° C. | 1:15:15 | 23.32% |
| 60 min | 130° C. | 1 | 30 min | 80° C. | 1:15:15 | 28.46% |
| 60 min | 150° C. | 1 | 30 min | 80° C. | 1:15:15 | 41.83% |

EXAMPLE 5

Solvent Variation in the Fractionation of Lipid Components from Microalgae

Four aliquots of 73.4 g (dry weight) of a *Nannochloropsis* sp. (the same sample was used in Examples 4 and 5) biomass was suspended with 1,101.0 g for making the mix ratio of 1:15 (or 440.4 g for 1:6) of water and the pH was adjusted to 1 with sulfuric acid. The aqueous suspension was pre-conditioned under 120° C. for 60 minutes with agitation. Then, 1,101.0 g for making the mix ratio of 1:15 (or 367.0 g for 1:5) of hexane was added to afford an fractionation mixture with the biomass:water:hexane ratio of 1:15:15, 1:15:5, 1:6:15, and 1:6:5. The lipid fractionation was performed in a positive displacement roller type pump for 30 minutes at 80° C. After fractionation, the aqueous phase and the hexane phase were separated by centrifugation. The lipid components fractionated by hexane was recovered by distillation of hexane. The aqueous biomass solution was fractionated once again using corresponding ratio of hexane. The lipids were combined and weighed for calculation of the yields. As shown in TABLE 4, the biomass:water:hexane ratio of 1:15:15 provided the highest lipid yield. However, when consumption of water and

TABLE 3A

| Pre-conditioning time | Pre-conditioning temperature | pH | Fractionation time | Fractionation temperature | Mix ratio (biomass:water:hexane) | Lipid Yield |
| --- | --- | --- | --- | --- | --- | --- |
| 60 min | 80° C. | 2 | 30 min | 80° C. | 1:15:15 | 18.38% |
| 60 min | 100° C. | 2 | 30 min | 80° C. | 1:15:15 | 19.76% |
| 60 min | 120° C. | 2 | 30 min | 80° C. | 1:15:15 | 16.09% |
| 60 min | 130° C. | 2 | 30 min | 80° C. | 1:15:15 | 18.45% |
| 60 min | 150° C. | 2 | 30 min | 80° C. | 1:15:15 | 16.57% | fractionating solvent needs to be taken into consideration especially for the large scale production of biofuel, the alternative solvent saving combination such as 1:6:5 (biomass:water:hexane) can be used.

TABLE 4

| Pre-conditioning time | Pre-conditioning temperature | pH | Fractionation time | Fractionation temperature | Mix ratio (biomass:water:hexane) | Lipid Yield |
|---|---|---|---|---|---|---|
| 60 min | 120° C. | 1 | 30 min | 80° C. | 1:15:15 | 28.18% |
| 60 min | 120° C. | 1 | 30 min | 80° C. | 1:15:5 | 24.34% |
| 60 min | 120° C. | 1 | 30 min | 80° C. | 1:6:15 | 25.01% |
| 60 min | 120° C. | 1 | 30 min | 80° C. | 1:6:5 | 21.87% |

EXAMPLE 6

Polar Solvent Variation in the Fractionation of Lipid Components from Microalgae A sample of *Nannochloropsis* sp. microalgae biomass (the same sample was used in Examples 2, 6, 7, and 8) containing 18.98% DWS was dried and pulverized in preparation for lipid fractionation (sample A). The dried sample was neither conditioned as demonstrated in Example 2, nor was polar solvent added. Non-polar solvent (hexane) was added to the dried microalgae, and the mixture was heated at 60° C. for 15 minutes with agitation as in Example 2. The sample was then transferred into a 1 liter hopper and mixed under high shear for a time of 15 minutes at 40° C. The phases were partitioned with heat and separated by centrifugation. The hexane was distilled and the high shear/partitioning/separation process was repeated to determine a lipid yield by two step fractionation.

EXAMPLE 7

Non-Polar Solvent Variation in the Fractionation of Lipid Components from Microalgae A *Nannochloropsis* sp. microalgae biomass samples (the same sample was used in Examples 2, 6, 7, and 8) containing 18.98% DWS were conditioned for fractionation by mixing water, the microalgae paste and acids. The sample was processed as described in Example 2 to complete the conditioning step. Hexane was added in the amount shown in the table. The mixture was transferred into a 1 liter hopper and mixed under high shear for a time of 15 minutes at 40° C. The phases were partitioned with heat and separated by centrifugation as described in Example 2. The lipid-containing hexane was distilled and the high shear/partitioning/separation process was repeated to determine a lipid yield by two-step fractionation on the sample.

TABLE 5

| Sample | Biomass Parts by weight | Weight % | Water (polar) Parts by Weight | Weight | Hexane (non-polar) Parts by Weight | Weight % | Yield % wt. |
|---|---|---|---|---|---|---|---|
| A | 1 | 3.02% | <0.5 | <1.51% | 31.61 | 95.47% | 0.96% |
| Control (Example 2) | 1 | 4.54% | 12.53 | 56.83% | 8.52 | 38.63% | 33.00% |

The dried sample (A) was compared to the control sample processed as described in Example 2. Results are summarized in TABLE 5.

As demonstrated, effective fractionations are not achieved at very low polar solvent concentrations such as in a dry aglal biomass used in Sample A The low percentage content non-polar solvent sample was compared to the control sample described in Example 2. Results are summarized in TABLE 6.

As demonstrated, very low amounts (<6% of the mixture) of non-polar solvent in the algae biomass/polar solvent mixture produce a poor lipid fractionation result.

TABLE 6

| Sample | Biomass Parts by weight | Weight % | Water, polar Parts by Weight | Weight | Hexane, non-polar Parts by Weight | Weight % | Yield % wt. |
|---|---|---|---|---|---|---|---|
| A | 1 | 6.94% | 12.53 | 86.95% | 0.88 | 6.11% | 11.47% |
| Control (Example 1) | 1 | 4.54% | 12.53 | 56.83% | 8.52 | 38.63% | 33.00% |

EXAMPLE 8

Variations in the Conditioning Step in the Fractionation of Lipid Components from Microalgae A *Nannochloropsis* sp. microalgae biomass sample (Sample A, TABLE 7) containing 18.98% DWS (the same sample was used in Examples 2, 6, 7, and 8) was conditioned for fractionation by mixing polar conditioning solvent (water), the microalgae and acids in the ratios as described in Example 2. The mixture was heated to 60° C. for 15 minutes as described in Example 2 to complete the conditioning step. The polar solution was then neutralized to a pH of 7.0 by the addition of sodium hydroxide. Non-polar solvent (hexane) was then added to the mixture as described in Example 2, and the mixture was transferred into a 1 liter hopper and mixed under high shear to contact the non-polar solvent for a time of 15 minutes at 40° C. The phases were partitioned with heat and separated by centrifugation. The lipid-containing hexane was distilled and the contacting/partitioning/separation process was repeated to determine a lipid yield by two step fractionation.

A second *Nannochloropsis* sp. microalgae biomass sample (Sample B, TABLE 7) containing 18.98% DWS was not conditioned prior to fractionation. The microalgae biomass was prepared by mixing polar conditioning solvent (water), and the microalgae as described in Example 2, except without acids. The mixture was not heated. Non-polar solvent (hexane) was added to the mixture as described in Example 2. The mixture was transferred into a 1 liter hopper and mixed under high shear to contact the non-polar solvent for a time of 15 minutes at 40° C. The phases were partitioned with heat and separated by centrifugation. The lipid-containing hexane was distilled and the contacting/partitioning/separation process was repeated to determine a lipid yield by two step fractionation.

Results are summarized in TABLE 7.

TABLE 7

| | Lipid Yield, % wt. |
|---|---|
| Control (Example 2) | 33.00% |
| Sample A, *Nannochloropsis* Lipid fractionation with conditioning followed by neutralization prior to contacting step with non-polar solvent | 21.40% |
| Sample B, *Nannochloropsis* Lipid fractionation without conditioning | 3.40% |

As demonstrated, elimination of the conditioning step results in ineffective fractionation. Preferably, the conditioning agent is carried through into the non-polar solvent contacting step.

EXAMPLE 9

Production of Semi-Volatile Organic Compounds (SVOC) and Other Organic Compounds Upon Microalgae Biomass Conditioning and Fractionation During the microalgae biomass conditioning and lipid fractionation, considerable amounts of SVOC and other organic compounds were identified through GC/MS (FIG. 5). Taking a sample of *Scenedesmus* sp. as an example, the fractionated algae oil was diluted with HPLC grade heptane to approximately 10,000 ppm (w/w). A 1.0 µl is injected in the GC/MS equipped with a column of HP-5MS 5% phenylmethyl siloxane, 30 meter, ID=0.250 mm, film thickness 0.25 µm. The split ratio was 1:50 with a flow of 1.5 ml/min of hydrogen carrier gas. Injector temperature was at 250° C. The initial oven temp was 40° C. for 3.0 minutes, then ramped at 5° C./min until 320° C. and held for 10 minutes. The GC/MS analysis of the fractionated microalgae oil demonstrated that these SVOC and other organic compounds accounted for 7.66% of total biocrude oil (FIG. 5). Further identity analysis based on their mass spectra indicated these compounds are a series of typical terpenoid and fatty acid degradation products including but not limited to toluene; xlyene; styrene; trimethyl-benzene; 2-ethyl-toluene; 1-methyl-3-propyl-benzene; tetramethyl-Benzene; methyl-propenyl-benzene; naphthalene; alkyl substituted naphthalene; heptadecane; heptadecene; isoprenoid fragments such as: 2,2,6,6-tetramethyl-heptane; 2,5,-dimethylheptane; 2,4,6-trimethylheptane; 3,3-dimethyl octane; 2,2,3-trimethylhexane; 2,2,6,6-tetramethylheptane; 2,2,3,4-tetramethylpentane; 2,2-dimethyldecane; 2,2,4,6,6-pentamethylheptane; 2,4,4-trimethylhexane; 4-methyldecene; 4-methyldecane; 3,6-dimethyloctane; 2,6-dimethylundecane; 2,2-dimethylheptane; 2,6,10-trimethyldodecane; 5-ethyl-2,2,3-trimethylheptane; 2,5,6-trimethyldecane; 2,6,11-trimethyldodecane and isomers of the afore listed compounds. Different amounts of semi-volatiles and hydrocarbons can be found in algae based on their treatment before harvesting, as well as process conditions of pH, temperature, and solvent ratios used in the steps of the present invention. Since both the semi-volatile organic compounds and these degradation organic compounds can be used as a component in jet fuel, the present invented process of biomass conditioning and fractionation represents an efficient way to produce high value jet fuel or jet fuel additive.

EXAMPLE 10 pH and Temperature Variation in the Microalgae Biomass Fractionation of Polar Components Upon twice lipid fractionation (biomass:water:hexane=1: 15:15) of the 120° C. pre-conditioned *Nannochloropsis* sp.

(the same sample was used in Examples 1, 10, 13, and 16) biomass at different pH, the post-fractionation aqueous biomass fraction comprised a layer of microalgae biomass slurry and a layer of clear aqueous solution, which presumably contain hydrolyzed protein products, carbohydrates, and other soluble polar components. To access the effectiveness of fractionation of carbohydrate and other polar components, the aqueous layer was subject to a carbohydrate composition analysis by following the NREL LAP 014 procedure. The composition of other polar components such as organic acids and glycerol in the aqueous solution was analyzed on an Agilent Aminex HPX-87H HPLC column using 0.02 M sulfuric acid as solvent. Similar to lipid fractionation, fractionation under strong acidic conditions (pH1 or 2) generated more sugars, organic acids, and glycerols (TABLE 8A). Surprisingly, the invented fractionation process is able to produce substantial amount of ethanol with an unknown mechanism, making the whole process more economically viable.

TABLE 8A

| pH | Glucose (g/l) | Cellobiose (g/l) | Xylose (g/l) | Galactose (g/l) | Arabinose (g/l) | Mannose (g/l) | Total Sugars (g/l) | Glycerol (g/l) | Total Organic Acid (g/l) | Ethanol (g/l) |
|---|---|---|---|---|---|---|---|---|---|---|
| 1 | 1.195 | 0.011 | 1.057 | 1.196 | 0.074 | 0.216 | 3.749 | 0.403 | 1.011 | 1.282 |
| 2 | 0.798 | 0 | 0.455 | 0.301 | 0 | 0.525 | 2.079 | 0.190 | 0.368 | 2.627 |
| 3 | 0.700 | 0 | 0.408 | 0.264 | 0 | 0.058 | 1.430 | 0.189 | 0.516 | 1.436 |
| 5 | 0.697 | 0 | 0.435 | 0.266 | 0 | 0.065 | 1.463 | 0.229 | 0.676 | 3.269 |
| 7 | 0.676 | 0 | 0.470 | 0.230 | 0 | 0.142 | 1.518 | 0.262 | 0.665 | 1.467 |

To test the effect of temperature toward the efficiency of fractionation of polar components, another *Nannochloropsis* sp. was pre-conditioned at 80 and 120° C. under pH2 and fractionated. Although the lipid yields were comparable to each other, it was evident that the 120° C. pre-conditioning led to a greater fractionation of carbohydrates and organic acids (TABLE 8B). Therefore, 120° C. is preferred to 80° C. in consideration of overall fractionation.

tionation processes under pH 1 and 2 did not efficiently fractionate sugars into aqueous solution. In contrast, the majority of sugars were still trapped by the microalgae biomass based on the carbohydrate composition analysis of the layer of biomass slurry (Table 9), suggesting some further post-fractionation steps such as enzyme hydrolysis is needed to release more carbohydrates in order to proceed to following applications (FIG. 3).

TABLE 8B

| Pre-conditioning temperature | pH | Mix ratio (biomass:water:hexane) | Lipid Yield | Total Carbohydrates (g/l) | Total Organic Acids (g/l) |
|---|---|---|---|---|---|
| 120° C. | 2 | 1:15:15 | 16.09% | 1.77 | 11.36 |
| 80° C. | 2 | 1:15:15 | 18.38% | 0.84 | 9.26 |

EXAMPLE 11

Additional Microalgal Biomass Fractionation of Polar Components

Example 10 showed the fractionation under pH 1 or 2 is capable of releasing significant amounts of sugars, organic acids, glycerols, and ethanol from the selected *Nannochloropsis* sp. biomass. In this example, an additional *Nannochloropsis* sp. (the same sample was used in Examples 11 and 12) was selected to test the efficiency of the polar component fractionation under pH 1 and 2. Upon a similar fractionation process as described in Example 10, the aqueous solution was analyzed using the NREL LAP 014 procedure. As result (Table 9), for this specific species of microalgae, both frac-

TABLE 9

| Sample | Glucose (g/l) | Xylose (g/l) | Galactose (g/l) | Arabinose (g/l) | Mannose (g/l) | Cellobiose (g/l) |
|---|---|---|---|---|---|---|
| pH 1 sample (biomass layer) | 2.70 | 0.12 | 2.43 | 0.00 | 0.74 | 0.00 |
| pH 1 sample (aqueous layer) | 0.41 | 0.00 | 0.43 | 0.08 | 0.08 | 0.00 |
| pH 2 sample (biomass layer) | 0.48 | 0.08 | 0.89 | 0.00 | 0.00 | 0.00 |
| pH 2 sample (aqueous layer) | 0.012 | 0.017 | 0.00 | 0.002 | 0.00 | 0.00 |

EXAMPLE 12

Enzymatic Hydrolysis of the Post-Fractionation Aqueous Biomass Fraction

Carbohydrates account for approximately 15-20% of microalgae DWS. A majority of carbohydrates exist as the structural components of cell wall and cell membrane in the forms of polysaccharides (mainly as glucan, galactan, and mannan in the selected microalgae Nannochloropsis sp. based on composition analysis), glycolipids, glycoproteins, and etc. Without fractionation and liberation into aqueous solution, this valued nutrient source cannot be taken advantage. However, the carbohydrate composition analysis shown in Example 11 demonstrated that the cell permeation conditioning with a combination of effects of acid, heat, mechanical shear, and organic solvent fractionation (hexane) led to an incomplete liberation of monosugars. Thus, further enzymatic hydrolysis of the post-fractionation aqueous fraction was carried out.

Using a combination of three commercial hydrolases (Novozymes) including the cellulase complex (NS50013), β-glucanase (NS50012), and β-glucosidase (NS50010), enzymatic hydrolysis of 1 liter of post-fractionation aqueous biomass fractions derived from pH1 and pH2 conditioning (see Example 3) were performed in a shaker incubator (150 rpm) at 50° C. and samples were taken every 24 hours. According to the sugar composition analysis of the hydrolyzed samples (TABLE 10), enzymatic hydrolysis released much greater amounts of glucose, cellobiose, galactose, and mannose, making the resultant aqueous biomass solution a better growth culture for either vegetative growth of heterotrophic microalgae to produce additional lipids and other high value products (Example 14) or yeast alcohol fermentation (Example 15).

TABLE 10

| Sample* | Glucose (g/l) | Cellobiose (g/l) | Xylose (g/l) | Galactose (g/l) | Arabinose (g/l) | Mannose (g/l) |
|---|---|---|---|---|---|---|
| pH 1, 0 h | 1.80 | 0 | 0 | 0.06 | 0 | 0.04 |
| pH 1, 24 h | 3.00 | 0 | 0 | 0.92 | 0 | 0.09 |
| pH 1, 48 h | 3.12 | 0.11 | 0 | 0.93 | 0 | 0.10 |
| pH 2, 0 h | 1.90 | 0 | 0 | 0.07 | 0 | 0.05 |
| pH 2, 24 h | 2.83 | 0 | 0 | 0 | 0 | 0.18 |
| pH 2, 48 h | 2.27 | 0.02 | 0 | 0.01 | 0 | 0.20 |

*The sample of post-fractionation biomass fraction with pH 1 treatment had an initial pH of 2. Therefore, its pH was adjusted to 5 with NaOH to optimize the activity of hydrolases. The sample of post-fractionation biomass fraction with pH 2 treatment had an initial pH of 5.5 and was directly subject to enzymatic hydrolysis.

The resultant hydrolyzed aqueous biomass for the two samples as processed above were then processed in the fractionation process to determine if additional biocrude oils could be recovered. Each sample had sulfuric acid added to it to return it to its original pH of 1 or 2. The pH adjusted samples were extracted for 30 minutes at 80° C. The biomass to hexane ratio was 1:10 and 1:15 for the 1 pH and 2 pH samples respectively with the samples yielding 7.70% and 12.6% additional biocrude oil on a dry weight basis of the residual biomass solids. This demonstrates that additional biocrude lipids can be recovered after enzyme hydrolysis treatment of the aqueous biomass fraction.

EXAMPLE 13

Phosphate Analysis of the Post-Extraction Aqueous Biomass Solution

Phosphorus is one of critical elements to microalgae growth. Fast growing microalgae to support large-scale biofuel production requires a great amount of supplement of inorganic phosphorus (organic phosphorus cannot be efficiently utilized by microalgae) that is often costly. This invented fractionation process not only effectively releases carbohydrates and proteins, but also efficiently turns organic phosphorus mainly existing as phospholipids into inorganic phosphate.

Upon a similar fractionation process as described in Example 3, the phosphate contents in the post-extraction aqueous biomass solution derived from a Nannochloropsis sp. (the same species was used in Examples 1, 10, 13, and 16) were measured by GC/MS analysis after a standard trimethylsilyl derivatization of phosphate. It was observed that more phosphate was released from phospholipids under more acidic pre-conditioning (TABLE 11). Without fractionation, in contrast, only a small amount of phosphate (1.91%) was found in the aqueous solution (TABLE 11). Thus, the present invention of microalgae biomass fractionation is capable of generating a nutrient sufficient and phosphorus rich post-fractionation solution as an excellent growth media for vegetative growth of heterotrophic microalgae for the production of additional lipids or other high value products (Example 14).

TABLE 11

| pH | $PO_4^{3-}$ (DW %) |
|---|---|
| 2 | 7.84% |
| 3 | 4.52% |
| 5 | 3.22% |
| 7 | 2.88% |
| 7 (without fractionation) | 1.91% |

EXAMPLE 14

Post-Extraction Aqueous Solution as a Nutrient-Sufficient Culture for Vegetative Growth of Heterotrophic Microalgae According to the composition analysis of the post-extraction aqueous solution, it contains substantial soluble carbohydrates, proteins, organic acids, phosphates and etc., showing its great potential to be developed into animal feed or growth media for microorganisms (e.g. yeasts, bacteria) or heterotrophic microalgae. Among these potential applications, it is particularly significant to use the nutrient rich post-extraction aqueous solution to support the fast growth of heterotrophic microalgae since they can quickly produce large amounts of additional lipids or other high value products under nutrient sufficient conditions.

TABLE 12A

| Medium # | 10X Proteose Media (ml) | Sterile LF (ml) | Sterile Water (ml) | Inoculum (ml) | Percent LF | Counts (Cells/ml) |
|---|---|---|---|---|---|---|
| 1 | 1.0 | 5.0 | 3.0 | 1.0 | 50 | 7,500,000 |
| 2 | 1.0 | 2.5 | 5.5 | 1.0 | 25 | 3,200,000 |
| 3 | 1.0 | 1.25 | 6.75 | 1.0 | 12.5 | 2,400,000 |
| 4 | 1.0 | 0.625 | 7.375 | 1.0 | 6.25 | 2,200,000 |
| 5 | 1.0 | 0.313 | 7.687 | 1.0 | 3.13 | 1,700,000 |
| 6 | 1.0 | 0.0 | 8.0 | 1.0 | 0 | 1,100,000 |

Figure 6:
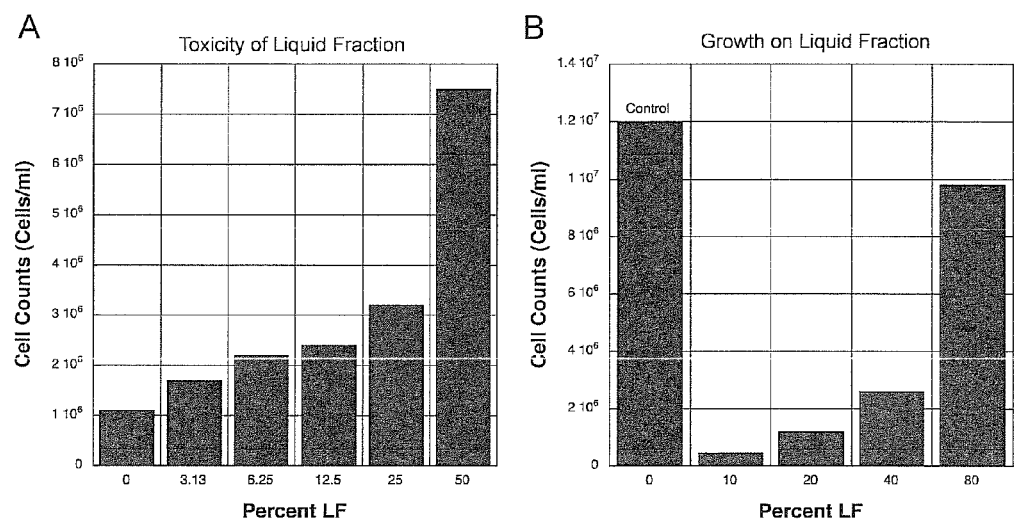
FIGS. 6A and 6B are diagrams of the post-fractionation aqueous solution as a medium to support heterotrophic growth of *Chlorella* sp.

To test the capability of the post-extraction aqueous solution (i.e. liquid fraction) derived from the selected Nannochloropsis sp. to support heterotrophic growth of a different microalgae, a toxicity evaluation of the aqueous solution was first performed. Specifically, one flask containing 50 ml of autoclaved 1× Proteose media (Bacto Peptone, 1 g/l;

K₂HPO₄, 75 mg/l; KH₂PO₄, 175 mg/l; NaNO₃, 250 mg/l; NaCl, 25 mg/l; MgSO₄.7H₂O, 305 mg/l; CaCl₂.H₂O, 170 mg/l) was inoculated with a loop of microalgae *Chlorella* sp. and rotated in the light for 48 hours at 28° C. Then, this seed culture was used to inoculate a set of tubes with varying amounts of liquid fraction (LF) from fractionation of *Nannochloropsis* biomass. For this specific experiment, the 40 ml of LF (derived from 2.67 g of biomass upon fractionation) was centrifuged at 5,000 g for 10 minutes to remove residual solids. The supernatant was adjusted to pH 7.0 with NaOH, and then filtered through a 0.22 μm sterile filter. Various amounts of the LF were added to make up the Proteose media in the tubes as described in Table 11A. The test tubes were placed in a shaker at 200 rpm, 28° C. and allowed to grow for 72 hours and the cell numbers of *Chlorella* sp. were determined using a hemocytometer. It was shown that the LF is nontoxic to the growth of *Chlorella* sp. (Table 12A and FIG. 6A). Next, using the 1× Proteose media as control, the LF was demonstrated to be able to support the heterotrophic growth of *Chlorella* sp. almost as well as the 1× Proteose media (Table 12B and FIG. 6B), indicating it is an effective microalgae growth media.

TABLE 12B

| Mudium # | 10X Proteose Media (ml) | Sterile LF (ml) | Sterile Water (ml) | Inoculum (ml) | Percent LF | Counts (Cells/ml) |
|---|---|---|---|---|---|---|
| 1 | 0.0 | 1.0 | 8.0 | 1.0 | 10 | 450,000 |
| 2 | 0.0 | 2.0 | 7.0 | 1.0 | 20 | 1,200,000 |
| 3 | 0.0 | 4.0 | 5.0 | 1.0 | 40 | 2,600,000 |
| 4 | 0.0 | 8.0 | 1.0 | 1.0 | 80 | 9,800,000 |
| 5 | 1.0 | 0.0 | 8.0 | 1.0 | 0 | 12,000,000 |

EXAMPLE 15

Ethanol Fermentation Using Aqueous Solution as Fermentation Media

Upon iterative fractionation performed twice, the aqueous solution containing soluble carbohydrates, proteins, and inorganic salts, together with biomass suspension that mainly includes debris of microalgae, insoluble proteins and carbohydrates, was pH neutralized, concentrated in the range of 26% by dry weight, and saccharified using commercially available enzymes (SPIRIZYME® (Novozymes), ACCELERASE® (Genecor)), and used as fermentation culture to support yeast ethanol fermentation. Notably, the neutralization step is not necessary when the pH of the polar biomass solution is between 5.0 and 7.0.

The chemical composition analysis demonstrated that carbohydrates in polar biomass solution account for 18% of the select *Nannochloropsis* sp. microalgae DWS. Together with the HPLC analysis of the saccharide composition of the concentrated post-fractionation aqueous solution showing the predominant sugar is glucose, which accounts for 36% of the total soluble carbohydrates (TABLE 13), it is anticipated that the post-fractionation solution should be suitable for the yeast ethanol fermentation.

Using this hydrolyzed post-fractionation biomass solution as fermentation media, the yeast strain *Saccharomyces cerevisiae* produced 9.3 g/l ethanol. Moreover, the sugar composition analysis (TABLE 13) demonstrated that other soluble carbohydrates include xylose (25%), arabinose (17%), cellobiose (8%), formic acid (7%), acetic acid (4%), and lactic acid (1%), showing its greater potential to support production of more ethanol provided that some engineered yeast strains that are able to use xylose, arabinose, or a combination of yeast strains are selected for alcohol production. Notably, the fermentation using a co-culture of yeasts *S. cerevisiae* and *Picheia stipidis* produced 13.6 g/l ethanol. The residual composition of major sugars in post-fermentation solution was shown in TABLE 13, indicating an almost complete exhaustion of saccharides.

TABLE 13

|  | Carbohydrates in Pre-fermentation Solution (% DW) | Carbohydrates in Post-fermentation Solution (% DW) |
|---|---|---|
| Glucose | 36.1% | 0.4% |
| Cellobiose | 8.0% | 0.3% |
| Xylose | 24.6% | 0.8% |
| Arabinose | 16.5% | 1.0% |
| Lactic acid | 1.0% | Not determined |
| Formic acid | 6.6% | Not determined |
| Acetic acid | 4.2% | Not determined |

The post-fermentation solution was found to contain significant lipid components, indicating the selected strain of yeast does not significantly metabolize the lipids from microalgae. To maximize the lipid productivity of the whole process, after removal of the produced ethanol during the fermentation by distillation and yeast cells, the post-fermentation fraction was recycled back to the fractionation tank for the iterative fractionation. After the additional fractionation, the lipids were almost completely fractionated and the lipid depleted aqueous solution was then subjected to the protein production (FIG. 3). It is evident that the microbial fermentation is capable of improving the total yield of lipid production by up to 20%. Likely, the fermentation is capable of facilitating the microalgae cell permeation to liberate more integrated lipid materials from microalgal cell membranes or cell walls.

EXAMPLE 16

Protein Composition Analysis of the Post-Fractionation Aqueous Biomass Fraction

Upon twice lipid fractionation (biomass:water:hexane=1:15:15) of the 120° C. pre-conditioned *Nannochloropsis* sp. (this species was identical to the one used in Example 1, 10, 13, and 16) biomass at pH 1, the post-fractionation aqueous biomass fraction comprised a layer of microalgae biomass slurry and a layer of clear aqueous solution, both of which presumably contain hydrolyzed protein products, carbohydrates, and other aqueous soluble components. To access the effectiveness of fractionation of protein products including proteins, hydrolyzed peptides, and free amino acids, the sample of aqueous layer was subject to protein composition analysis.

TABLE 14

| Amino Acid | % DW |
|---|---|
| Tryptophan | 0.10%* |
| Cysteine | 0.10% |
| Methionine | 0.10% |
| Aspartate | 0.45% |
| Threonine | 0.10% |
| Serine | 0.10% |
| Glutamate | 0.75% |

TABLE 14-continued

| Amino Acid | % DW |
| --- | --- |
| Alanine | 0.60% |
| Proline | 0.66% |
| Glycine | 0.30% |
| Valine | 0.15% |
| Isoleucine | 0.10% |
| Leucine | 0.30% |
| Tyrosine | 0.10% |
| Phenylalanine | 0.15% |
| Lysine | 0.15% |
| Histidine | 0.10% |
| Arginine | 0.15% |
| Total (% DWS) | 4.46% |

*All numbers of 0.10% represent an upper limit of the percentage of the corresponding amino acid since the amounts of these amino acids were lower than the detection limit of the selected method. All other percentage numbers greater than 0.10% represent the real concentrations of amino acids.

Following the method references Free Amino Acid Profile—AOAC 999.13 mod. and Free Tryptophan—AOAC 999.13 mod., the composition analysis (TABLE 14) demonstrated that the fractionated soluble protein products account for 4.46% (dry weight solid, DWS) of biomass and the protein products from this *Nannochloropsis* sp. are a good source for production of glutamate, aspartate, alanine, and proline. This post-fractionation biomass fraction containing rich carbohydrates and proteins can be returned to the fermentation step in support of the growth of yeasts or fed to the growth of heterotrophic microalgae (FIGS. 3 and 4). Alternatively, to produce higher valued protein products, the post-fractionation fraction was first treated with hot alkali at pH=11.4 at a temperature of 80° C. to solubilize the proteins. Subsequently, the acidification using sulfuric acid at 35° C. to pH 5.5 and cooling of the high protein solution precipitated the majority of microalgae proteins. The precipitates were separated from solution with filtration to provide protein products, which can be used for production of aquaculture or animal feed or higher valued amino acids.

EXAMPLE 17

Pulse Electric Field (PEF) Application in Conditioning Step in the Fractionation of Lipid Components from Microalgae One aliquot of 49.6 g (dry weight, DW) of a *Nannochloropsis* sp. (a different sample from those used in prior examples) biomass was suspended with 992.0 g of water and the pH was adjusted to 1 with sulfuric acid. The aqueous suspension was pre-conditioned using a prototype pulse electric field (PEF) transducer (Diversified Technologies Inc. prototype continuous flow transducer with a DTI Model HPM20-150 High Power Modulator and a BK Precision 4030 10 MHz Pulse generator) under recirculation flow to the reactor for 20 minutes at 31.5° C. at 8.5 KV and 150 Hz.

Then, 744.0 g of hexane was added to afford an fractionation mixture with the biomass:water:hexane ratio of 1:20:15. The lipid fractionation was performed in a positive displacement roller type pump for 30 minutes at 80° C. After fractionation, the aqueous phase and the hexane phase were separated by centrifugation. The lipid components fractionated by hexane was recovered by distillation of hexane. The aqueous biomass solution was fractionated once again by following an identical procedure. The lipids were combined and weighed for calculation of the yields.

The biomass yielded a 21.93% yield of biocrude lipids which is comparable to the thermal conditioning step for this type of algae. This example shows that PEF conditioning can be used in the invention to produce fractionation of the algae biomass and yield biocrude products.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, the invention may be practiced otherwise than as specifically described.

What is claimed is:

1. A method of fractionating algae, including the steps of: permeability conditioning whole algae suspended in a solution pH adjusted to a range chosen from the group consisting of 1.0 to 6.5 and 7.5 to 14 of at least one water-based polar solvent effecting the cell wall permeability of the algae to form a conditioned biomass, intimately contacting the conditioned biomass with at least one non-polar solvent and obtaining a multiphase suspension, partitioning the multiphase suspension to obtain a non-polar solvent solution and a polar biomass solution, recovering cell products from the non-polar solvent solution and polar biomass solution and fractionating polar and water soluble components from the biomass.

2. The method of claim 1, wherein said permeability conditioning step is further defined as adding an acid to the biomass wherein the pH is adjusted to a range of 1.0 to 6.5.

3. The method of claim 2, wherein the acid is chosen from the group consisting of acetic acid, hydrochloric acid, nitric acid, phosphoric acid, sulfuric acid, boric acid, hydrofluoric acid, hydrobromic acid, lactic acid, formic acid, propionic acid, carbon dioxide, and a mixture thereof.

4. The method of claim 1, wherein said permeability conditioning step is further defined as adding a base to the biomass wherein the pH is adjusted to a range of 7.5 to 14.

5. The method of claim 4, wherein the base is chosen from the group consisting of sodium hydroxide, potassium hydroxide, calcium hydroxide, alkali metals, alkaline earth metals, ammonium hydroxide, ammonia, sodium carbonate, potassium carbonate, boron hydroxide, aluminum hydroxide, borax, amino alcohols such as ethanol amine, diethanolamine, triethanol amine, isopropanolamine, diisopropylamine, triisopropylamine, propylamine, 2-propylamine, methylamine, dimethylamine, trimethylamine, dimethylethanol amine, monoethylethanolamine, 2-(2-aminoethoxy) ethanol, diglycolamines, diethylamine, and a mixture thereof.

6. The method of claim 1, wherein the polar solvent is a combination of water and one or more polar solvents chosen from the group consisting of low molecular weight aldehydes, ketones, fatty acids, methanol, ethanol, propanol, butanol, formic acid, acetic acid, propionic acid, and amphipathic solvents.

7. The method of claim 1, wherein said permeability conditioning step further includes the step of heating the biomass to a range of temperature chosen from the group consisting of about 25° C. to about 200° C., of about 45° C. to about 150° C., of about 55° C. to about 140° C., and of about 60° C. to about 130° C.

8. The method of claim 1, wherein said permeability conditioning step further includes a treatment chosen from the group consisting of mechanical treatment, electrical treatment, osmotic shock, infection with a lytic virus, exposure to elevated pressure, rapid pressure oscillation conditions, vacuum and pressure oscillation, and combinations thereof.

9. The method of claim 8, wherein said permeability conditioning step further includes the step of subjecting the biomass to low voltage pulse electric fields selected from the group including voltage from 1 to 150 volts, and voltage from 150 to 9000 volts.

10. The method of claim 1, wherein said permeability conditioning step further includes addition of enzymes chosen from the group consisting of endoglucanases, exoglucanases, cellobiohydrolases, β-glucosidase, endoxylanases, β-xylosidases, β-mannosidase, galactomannan-degrading enzymes, pectin lyases, pectate lyases, endopolygalacturonase-II, arabinofuranosidases, arabinoxylan, arabinofuranohydrolases, α-gucuronidases, feruloyl and p-coumaroyl esterases, cellulases, lipases, hemicellulase, pectinase and algaenan.

11. The method of claim 1, wherein the non-polar solvent is chosen from the group consisting of carbon dioxide, carbon tetrachloride, chloroform, cyclohexane, 1,2-dichloroethane, dichloromethane, diethyl ether, dimethyl formamide, ethyl acetate, propane, butane isomers, pentane isomers, hexane isomers, heptane isomers, octane isomers, nonane isomers, decane isomers, methyl-tert-butyl ether, toluene, butene isomers, pentene isomers, hexane isomers, heptene isomers, octene isomers, nonene isomers, decene isomers, mineral spirits, and 2,2,4-trimethylpentane.

12. The method of claim 11, wherein the polar solvent includes an alcohol chosen from the group consisting of amyl alcohols, propanols, and butanols.

13. The method of claim 1, wherein said partitioning step is further defined as separating the non-polar solvent solution from the polar biomass solution and a residual biomass by a process chosen from the group consisting of centrifugation, coalesce, decantation, variation in pressure, high flux membranes, ultrasonification, and heating.

14. A method of fractionating algae, including the steps of: permeability conditioning whole algae suspended in a pH adjusted solution of at least one water-based polar solvent with at least one enzyme to form a conditioned biomass, contacting the conditioned biomass with at least one non-polar solvent, partitioning to obtain a non-polar solvent solution and a polar biomass solution, and obtaining an end product selected from the group consisting of biocrude, soluble monosaccharides, disaccharides, oligosaccharides, polysaccharides, glycerols, amino acids, soluble proteins, peptides, fiber, nutrients, phosphocholine, phosphate, growth media, and residual solid algae cell structural particles, said permeability conditioning uses enzyme hydrolysis from the group consisting of endoglucanases, exoglucanases, cellobiohydrolases, β-glucosidase, endoxylanases, β-xylosidases, β-mannosidase, galactomannan-degrading enzymes, pectin lyases, pectate lyases, endopolygalacturonase-II, arabinofuranosidases, arabinoxylan, arabinofuranohydrolases, α-gucuronidases, feruloyl and p-coumaroyl esterases, cellulases, lipases, hemicellulase, pectinase and algaenan.

* * * * *